(12) United States Patent
Strong et al.

(10) Patent No.: US 7,741,113 B2
(45) Date of Patent: Jun. 22, 2010

(54) CELL-SPECIFIC MOLECULE AND METHOD FOR IMPORTING DNA INTO OSTEOBLAST NUCLEI

(75) Inventors: Donna D. Strong, Loma Linda, CA (US); Thomas A. Linkhart, Loma Linda, CA (US); David A. Dean, Chicago, IL (US)

(73) Assignees: Loma Linda University, Loma Linda, CA (US); The United States Government as represented by the Department of Veterans Affairs, Washington, DC (US); Northwestern University, Evanston, IL (US); University of South Alabama, Mobile, AL (US)

( * ) Notice: Subject to any disclaimer, the term of this patent is extended or adjusted under 35 U.S.C. 154(b) by 583 days.

(21) Appl. No.: 11/410,579

(22) Filed: Apr. 24, 2006

(65) Prior Publication Data

US 2006/0242725 A1    Oct. 26, 2006

Related U.S. Application Data

(60) Provisional application No. 60/674,881, filed on Apr. 25, 2005.

(51) Int. Cl.
C07H 21/02 (2006.01)
C07H 21/04 (2006.01)
C12N 5/00 (2006.01)
C12N 15/63 (2006.01)

(52) U.S. Cl. ............... 435/325; 536/24.1; 536/23.1; 435/320.1

(58) Field of Classification Search ............ 514/14; 536/23.1, 24.1; 435/320.1, 325
See application file for complete search history.

(56) References Cited

U.S. PATENT DOCUMENTS

| | | | |
|---|---|---|---|
| 5,827,705 | A | 10/1998 | Dean |
| 6,130,207 | A | 10/2000 | Dean et al. |
| 6,518,063 | B1 * | 2/2003 | Ducy et al. ............... 435/325 |
| 2003/0152560 | A1 | 8/2003 | Selden et al. |

OTHER PUBLICATIONS

Antoniv et al, (JBC, 276(24): 21754-21764, 2001.*
Akai et al, (Connective Tissue, 30: 1-6, 1998.*
Komori et al, (Journal of Cellular Biochemistry, 95: 445-453, 2005, available online Mar. 24, 2005.*
Akai et al (Gene, 239: 65-73, 1999.*
Choi et al, [PNAS 98(15): 8650-8655, 2001)].*
Dacquin et al., "Mouse alphal(I)-collagen promoter is the best known promoter to drive efficient Cre recombinase expression in osteoblast," *Dev Dyn.*, 224(2):245-251, 2002.
Dean et al., "Sequence requirements for plasmid nuclear import," *Exp. Cell Res.*, 253(2):713-722, 1999.
Strong et al., "Development of an osteoblast-specific DNA nuclear targeting sequence from the human type I alpha 2 procollagen promoter for development of efficient plasmid expression vectors," *Journal of Bone and Mineral Research*, 20(9) Supp. 1:S354, 2005.
Vacik et al., "Cell-specific nuclear import of plasmid DNA," *Gene Therapy*, 6(6):1006-1014, 1999.
Young et al., "Effect of a DNA nuclear targeting sequence on gene transfer and expression of plasmids in the intact vasculature," *Gene Therapy*, 10(17):1465-1470, 2003.
Genbank, Accession Nos. NM_000089.
Genbank® Accession No. AB013356.
Genseq Database Accession No. ADH54462.
EMBL Database Accession No. AF004877.
EMBL Database Accession No. AY090738.

* cited by examiner

*Primary Examiner*—Anne-Marie Falk
*Assistant Examiner*—Magdalene K Sgagias
(74) *Attorney, Agent, or Firm*—Klarquist Sparkman, LLP

(57) ABSTRACT

A plasmid, viral or linear DNA molecule containing a nucleic acid sequence derived from the promoter region of the hCol1α2 gene, which is selectively transported into the nuclei of cells in the osteoblast lineage. The sequence can be used independently as a nuclear entry sequence only, and/or as a nuclear entry sequence without regard to position, in a vector or linear DNA that directs gene expression and nuclear entry. The disclosure further includes a chimeric DNA sequence derived by the addition of osteoblast-specific enhancer sequences to the nuclear entry sequence/promoter sequence, to increase osteoblast-specific expression while retaining osteoblast-specific nuclear import. An enhancer sequence is derived from the promoter region of the human Core Binding Factor alpha 1 (Cbfa1/Runx2) gene. The Cbfa1/Runx2 promoter can be added to the sequence derived from, or alternatively, comprising the promoter region of the hCol1α2 gene. Also provided are methods of use of the novel sequences.

10 Claims, 6 Drawing Sheets

FIG. 1

SEQUENCE LISTING

<160> NUMBER OF SEQ ID NOS: 30

<210> SEQ ID NO 1
<211> LENGTH: 312
<212> TYPE: DNA
<213> ORGANISM: Homo sapiens

<400> SEQUENCE: 1
tgcagacaac gagtcagagt ttccccttga aagcctcaaa agtgtccacg tcctcaaaaa      60
gaatggaacc aatttaagaa gccagccccg tggccacgtc ccttccccca ttcgctccct     120
cctctgcgcc cccgcaggct cctcccagct gtggctgccc gggcccccag ccccagccct     180
cccattggtg gaggcccttt tggaggcacc ctagggccag ggaaactttt gccgtataaa     240
tagggcagat ccgggcttta ttattttagc accacggcag caggaggttt cggctaagtt     300
ggaggtactg gc                                                         312

<210> SEQ ID NO 2
<211> LENGTH: 111
<212> TYPE: DNA
<213> ORGANISM: Artificial sequence
<220> FEATURE:
<223> OTHER INFORMATION: recombinant enhancer

<400> SEQUENCE: 2
ctgctctaca aatgcttaac cttacaggag tttgggctcc ttcagcattt gtattctatc      60
caaatcctca tgagtcacaa aaattaaaaa gctatatcct tctggatgcc a              111

<210> SEQ ID NO 3
<211> LENGTH: 112
<212> TYPE: DNA
<213> ORGANISM: Artificial sequence
<220> FEATURE:
<223> OTHER INFORMATION: recombinant enhancer

<400> SEQUENCE: 3
gtttgggctc cttcagcatt tgtattctat ccaaatcctc atgagtcaca aaattaaaa       60 agctatatcc ttctggatgc caggaaaggc cttaccacaa gccttttgtg ag             112

<210> SEQ ID NO 4
<211> LENGTH: 111
<212> TYPE: DNA
<213> ORGANISM: Artificial sequence
<220> FEATURE:
<223> OTHER INFORMATION: recombinant enhancer

<400> SEQUENCE: 4
ctgctctaca aatgcttaac cttacaggag tttgggctcc ttcagcgcct gtattctatc      60
caaatcctca tgagtcacaa aaattaaaaa gctatatcct tctggatgcc a              111

<210> SEQ ID NO 5
<211> LENGTH: 10
<212> TYPE: DNA
<213> ORGANISM: Artificial sequence
<220> FEATURE:
<223> OTHER INFORMATION: Kozak sequence

<400> SEQUENCE: 5 gccgccatgr                                                             10

```
<210> SEQ ID NO 6
<211> LENGTH: 20
<212> TYPE: DNA
<213> ORGANISM: Artificial sequence
<220> FEATURE:
<223> OTHER INFORMATION: oligonucleotide primer

<400> SEQUENCE: 6
gtttgggctc cttcagcatt                                              20

<210> SEQ ID NO 7
<211> LENGTH: 20
<212> TYPE: DNA
<213> ORGANISM: Artificial sequence
<220> FEATURE:
<223> OTHER INFORMATION: oligonucleotide primer

<400> SEQUENCE: 7
ctgctctaca aatgcttaac                                              20

<210> SEQ ID NO 8
<211> LENGTH: 20
<212> TYPE: DNA
<213> ORGANISM: Artificial sequence
<220> FEATURE:
<223> OTHER INFORMATION: oligonucleotide primer

<400> SEQUENCE: 8
tggcatccag aaggatatag                                              20

<210> SEQ ID NO 9
<211> LENGTH: 20
<212> TYPE: DNA
<213> ORGANISM: Artificial sequence
<220> FEATURE:
<223> OTHER INFORMATION: oligonucleotide primer

<400> SEQUENCE: 9
ctcacaaaag gcttgtggta                                              20

<210> SEQ ID NO 10
<211> LENGTH: 26
<212> TYPE: DNA
<213> ORGANISM: Artificial sequence
<220> FEATURE:
<223> OTHER INFORMATION: oligonucleotide primer

<400> SEQUENCE: 10
cgtcgactcc ggatcgatcc tgagaa                                       26

<210> SEQ ID NO 11
<211> LENGTH: 27
<212> TYPE: DNA
<213> ORGANISM: Artificial sequence
<220> FEATURE:
<223> OTHER INFORMATION: oligonucleotide primer

<400> SEQUENCE: 11
gtctagataa ccagcacgtt gcccagg                                      27

<210> SEQ ID NO 12
<211> LENGTH: 28
<212> TYPE: DNA
<213> ORGANISM: Artificial sequence
<220> FEATURE:
<223> OTHER INFORMATION: oligonucleotide primer
```

```
<400> SEQUENCE: 12
ggtcgacctc tatcgatagg taccctag                                              28

<210> SEQ ID NO 13
<211> LENGTH: 28
<212> TYPE: DNA
<213> ORGANISM: Artificial sequence
<220> FEATURE:
<223> OTHER INFORMATION: oligonucleotide primer

<400> SEQUENCE: 13
gcgtcgacgc cagtacctcc aacttagc                                              28

<210> SEQ ID NO 14
<211> LENGTH: 20
<212> TYPE: DNA
<213> ORGANISM: Artificial sequence
<220> FEATURE:
<223> OTHER INFORMATION: oligonucleotide primer

<400> SEQUENCE: 14
tggccttccg tgttcctacc                                                       20

<210> SEQ ID NO 15
<211> LENGTH: 20
<212> TYPE: DNA
<213> ORGANISM: Artificial sequence
<220> FEATURE:
<223> OTHER INFORMATION: oligonucleotide primer

<400> SEQUENCE: 15
ttactccttg gaggccatgt                                                       20

<210> SEQ ID NO 16
<211> LENGTH: 21
<212> TYPE: DNA
<213> ORGANISM: Artificial sequence
<220> FEATURE:
<223> OTHER INFORMATION: oligonucleotide primer

<400> SEQUENCE: 16
caccacggca gcaggaggtt t                                                     21

<210> SEQ ID NO 17
<211> LENGTH: 20
<212> TYPE: DNA
<213> ORGANISM: Artificial sequence
<220> FEATURE:
<223> OTHER INFORMATION: oligonucleotide primer

<400> SEQUENCE: 17
ggcaggatga tgaccaggat                                                       20

<210> SEQ ID NO 18
<211> LENGTH: 20
<212> TYPE: DNA
<213> ORGANISM: Artificial sequence
<220> FEATURE:
<223> OTHER INFORMATION: oligonucleotide primer

<400> SEQUENCE: 18
gatcttacgc gtgctagccc                                                       20
```

```
<210> SEQ ID NO 19
<211> LENGTH: 20
<212> TYPE: DNA
<213> ORGANISM: Artificial sequence
<220> FEATURE:
<223> OTHER INFORMATION: oligonucleotide primer

<400> SEQUENCE: 19
ggcaggatga tgaccaggat                                              20

<210> SEQ ID NO 20
<211> LENGTH: 20
<212> TYPE: DNA
<213> ORGANISM: Artificial sequence
<220> FEATURE:
<223> OTHER INFORMATION: oligonucleotide primer

<400> SEQUENCE: 20
cacactgctg ctcatcactt                                              20

<210> SEQ ID NO 21
<211> LENGTH: 20
<212> TYPE: DNA
<213> ORGANISM: Artificial sequence
<220> FEATURE:
<223> OTHER INFORMATION: oligonucleotide primer

<400> SEQUENCE: 21
gctaagcaga tgtgcctgtt                                              20

<210> SEQ ID NO 22
<211> LENGTH: 20
<212> TYPE: DNA
<213> ORGANISM: Artificial sequence
<220> FEATURE:
<223> OTHER INFORMATION: oligonucleotide primer

<400> SEQUENCE: 22
tgcctgcatt accggtcgat                                              20

<210> SEQ ID NO 23
<211> LENGTH: 20
<212> TYPE: DNA
<213> ORGANISM: Artificial sequence
<220> FEATURE:
<223> OTHER INFORMATION: oligonucleotide primer

<400> SEQUENCE: 23
ggaccgacga tgaagcatgt                                              20

<210> SEQ ID NO 24
<211> LENGTH: 21
<212> TYPE: DNA
<213> ORGANISM: Artificial sequence
<220> FEATURE:
<223> OTHER INFORMATION: oligonucleotide primer

<400> SEQUENCE: 24
caagctggtg gctggaccaa t                                            21

<210> SEQ ID NO 25
<211> LENGTH: 22
<212> TYPE: DNA
<213> ORGANISM: Artificial sequence
<220> FEATURE:
<223> OTHER INFORMATION: oligonucleotide primer
```

```
<400> SEQUENCE: 25
catatgtcct tccgagtgag ag                                    22

<210> SEQ ID NO 26
<211> LENGTH: 24
<212> TYPE: DNA
<213> ORGANISM: Artificial sequence
<220> FEATURE:
<223> OTHER INFORMATION: oligonucleotide primer

<400> SEQUENCE: 26
cccaaagtcg ctctgagttg ttat                                  24

<210> SEQ ID NO 27
<211> LENGTH: 21
<212> TYPE: DNA
<213> ORGANISM: Artificial sequence
<220> FEATURE:
<223> OTHER INFORMATION: oligonucleotide primer

<400> SEQUENCE: 27
ggagcgggag aaatggatat g                                     21

<210> SEQ ID NO 28
<211> LENGTH: 21
<212> TYPE: DNA
<213> ORGANISM: Artificial sequence
<220> FEATURE:
<223> OTHER INFORMATION: oligonucleotide primer

<400> SEQUENCE: 28
gcgaagagtt tgtcctcaac c                                     21

<210> SEQ ID NO 29
<211> LENGTH: 20
<212> TYPE: DNA
<213> ORGANISM: Artificial sequence
<220> FEATURE:
<223> OTHER INFORMATION: oligonucleotide primer

<400> SEQUENCE: 29
tcgagacaac gagtcagagt                                       20

<210> SEQ ID NO 30
<211> LENGTH: 20
<212> TYPE: DNA
<213> ORGANISM: Artificial sequence
<220> FEATURE:
<223> OTHER INFORMATION: oligonucleotide primer

<400> SEQUENCE: 30
gccagtacct ccaacttagc                                       20
```

CELL-SPECIFIC MOLECULE AND METHOD FOR IMPORTING DNA INTO OSTEOBLAST NUCLEI

CROSS REFERENCE TO RELATED APPLICATION

This application claims priority to U.S. Provisional Application No. 60/674,881, filed Apr. 25, 2005, the disclosure of which is incorporated herein in its entirety.

STATEMENT REGARDING FEDERALLY SPONSORED RESEARCH

Research for the present disclosure was supported by grants from the National Medical Technology Testbed, and a Special Congressional Award to the Musculoskeletal Disease Center at the VA Loma Linda Healthcare System and was conducted in part at research facilities within the VA Loma Linda Healthcare System. Accordingly, the United States government has certain rights in the invention.

FIELD OF THE DISCLOSURE

The present disclosure relates generally to compositions and methods for the importing of DNA into the nuclei of a specific cell type to increase the efficiency of gene transfer and expression. In particular, the present disclosure provides methods and compositions for specifically targeting to and expression in the nuclei of osteoblasts.

BACKGROUND

The promise and potential of gene therapy to cure or alleviate symptoms in a variety of disorders and diseases has stimulated intensive research into new methods for transferring genes into cells. Gene therapy delivered by non-viral plasmid vectors or as linear DNA molecules has been only partially effective in animals and in a clinical setting because of technical difficulties. These difficulties arise from (1) cellular barriers to entry of DNA across the plasma membrane into the cytoplasm, (2) barriers to traversing the cytoplasm intact, and (3) barriers to nuclear entry.

In many targets of gene therapy, it is desirable to transfer and express therapeutic genes only in one cell type within a tissue. Three different approaches have been described for such cell-specific gene expression. First, the delivery of genes to certain cell types is based on the site and physical method of delivery. In other words, by injecting DNA into the big toe, gene transfer will occur mainly in the big toe, not the eye.

The second approach, which has been more widely utilized is to employ cell-specific gene promoters and enhancers to drive gene expression only in desired cell types. In this case, DNA is delivered to all cells within the tissue (or to as many cells as the delivery method allows), and gene expression is limited to those cells in which the promoter is active.

A third way to limit gene expression to certain cell types is to limit nuclear import of the plasmid DNA to certain cell types. Without nuclear import, there is no gene expression and the plasmid or linear gene delivery vehicle is degraded in the cytoplasm. It has been established that the nuclear envelope is one of the major barriers to gene transfer. In non-dividing cells, the nucleus is surrounded by a double membrane envelope that is impermeable to large nucleic acid molecules such as plasmid vectors or linear DNA molecules, which, unlike many proteins, lack discrete signals for nuclear import. Entry of large DNA molecules into the nucleus is very inefficient until the cell enters mitosis and the nuclear membrane temporarily breaks apart.

Specific polynucleotide sequences that facilitate nuclear entry have been identified, however, these sequences have only been successful at targeting entry into the nucleic of certain types of non-dividing cells. For example, a 72 base pair SV40 viral DNA sequence has been shown to facilitate entry of plasmids into the nuclei of a variety of cell types (Dean, *Exp Cell Res* 253:713, 1999; U.S. Pat. No. 5,827,705).

A sequence present in the smooth muscle gamma actin promoter is a mammalian gene sequence that was recently discovered to possess intrinsic nuclear entry activity. Because the smooth muscle gamma actin promoter DNA binds to a collection of transcription factors only expressed in smooth muscle cells, the DNA sequence mediates nuclear import selectively in smooth muscle cells. In transfection studies, incorporation of this sequence into a plasmid expression vector increases smooth muscle-specific gene transfer and expression; no expression is seen in non-smooth muscle cells. This sequence functions both in cultured cells and for smooth muscle cell selective gene delivery in animals (Vacik et al., *Gene Therapy* 6:1006, 1999; Dean, U.S. Pat. No. 6,130,207).

The common feature to these nuclear entry or import sequences is that they contain binding sites for transcription factors that in turn harbor protein signals known as nuclear localization signals (NLS) that interact with the cell's machinery for nuclear protein import.

However, to date no such nuclear targeting sequences have been identified that are capable of directing entry into the nuclei of osteoblast lineage cells involved in bone growth and regeneration.

SUMMARY OF THE DISCLOSURE

The present disclosure relates to compositions and methods for importing nucleic acids, such as DNA, into the nuclei of osteoblast lineage cells (the bone forming cells of the skeleton). A polynucleotide sequence that promotes transport of a nucleic acid into the nucleus of osteoblast lineage cells is disclosed. A DNA sequence which accomplishes this result is referred to herein as an "osteoblast specific nuclear targeting sequence," or "osteoblast specific nuclear entry sequence." For example, a polynucleotide sequence from the promoter region of the human type I alpha 2 procollagen (hCol1α2) gene overcomes the barrier to nuclear entry, efficiently transporting nucleic acids containing this sequence specifically into the osteoblast nucleus without the need for cell division.

Thus, one aspect of the disclosure relates to isolated or recombinant nucleic acids including an osteoblast-specific nuclear targeting sequence. An exemplary osteoblast specific nuclear targeting sequence is provided in SEQ ID NO:1. Vectors and cells incorporating such nucleic acids are also described. The disclosure also provides methods, employing osteoblast specific nuclear targeting sequences, for introducing nucleic acids into the nuclei of osteoblast lineage cells. Optionally such introduced nucleic acids are expressed to produce an RNA or polypeptide product. Kits for introducing nucleic acids into osteoblast lineage cells are also described. Methods for identifying agents that exert a genetic, physiologic, or phenotypic effect on osteoblast lineage cells are also a feature of the disclosure.

BRIEF DESCRIPTION OF THE DRAWINGS

FIG. 1 is a sequence comparison of the DNA structure of the hCol1a2 promoter regions in multiple species, and illustrates the conserved control elements that contribute to nuclear entry activity and robust basal expression in osteoblasts.

BRIEF DESCRIPTION OF THE SEQUENCE LISTING

Figure 2:
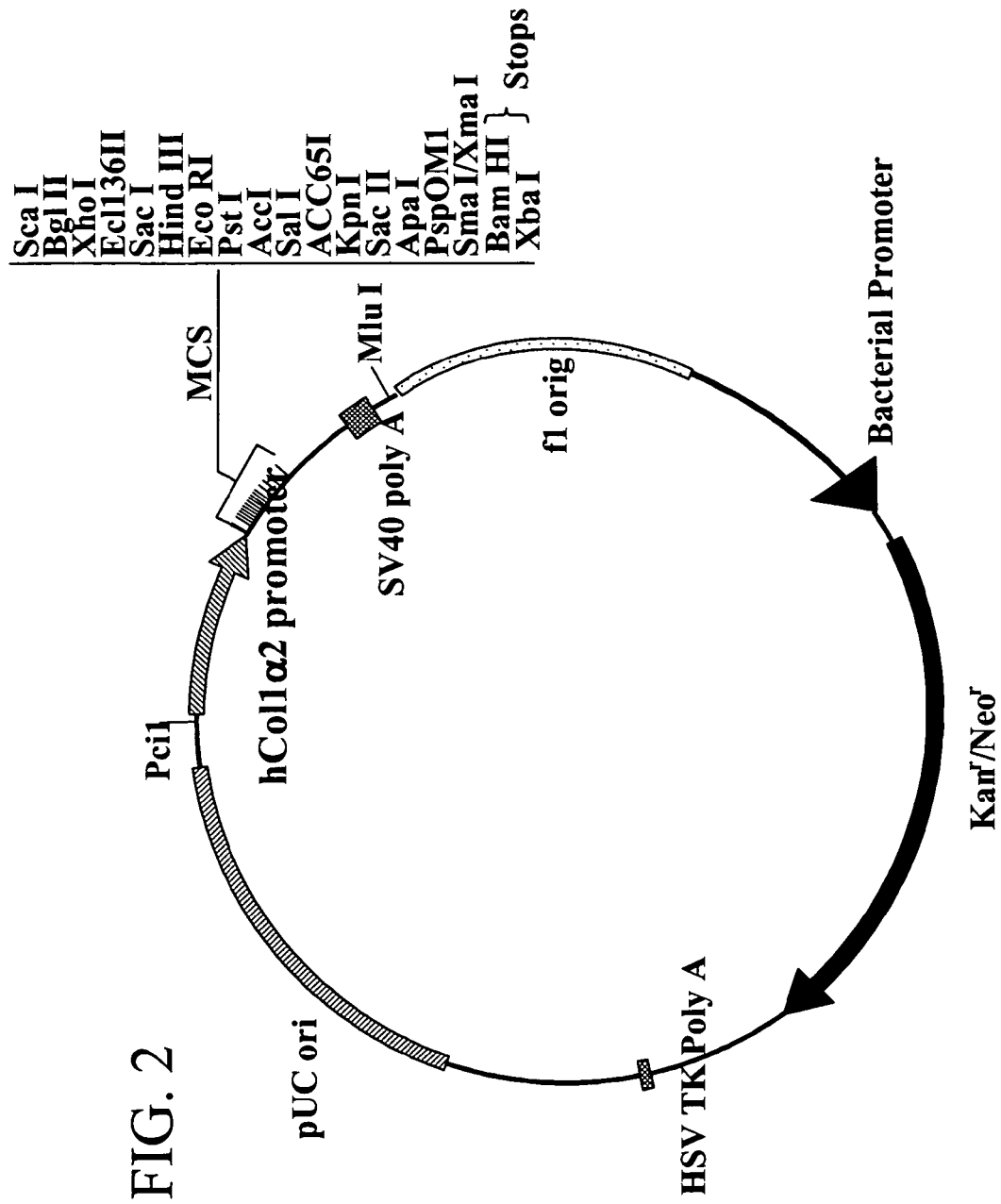
FIG. 2 is a schematic illustration of a plasmid expression vector with osteoblast-specific nuclear entry activity.

SEQ ID NO:1 represents position −267 through position +45 of a human alpha2(I) (pro)collagen gene (hCol1α2) promoter. Nucleotide positions are designated relative to the transcriptional start site (+1).

SEQ ID NOS:2-4 represent the sequences of osteoblast-specific enhancers.

SEQ ID NO:5 is the nucleotide sequence of an exemplary Kozak initiation site sequence.

SEQ ID NOs:6-9 are the nucleotide sequence of primers FP1, RP4, FP2 and RP3, respectively.

SEQ ID NOs:10 and 11 are nucleotide sequences of 5' and 3' primers for amplification of the rabbit β-globin intron.

SEQ ID NOs:12 and 13 are nucleotide sequences of 5' and 3' primers for amplification of the hRunx2-hCol1α2, respectively.

SEQ ID NOs:14 and 15 are the nucleotide sequences of primers for the amplification of GAPDH.

SEQ ID NOs:16-25 are the nucleotide sequences of primers for genotyping transgenic mice with osteoblast specific CRE recombinase transgenes.

SEQ ID NOs:26-28 are the nucleotide sequences for genotyping transgenic mice with the ROSA26 Reporter Gene.

SEQ ID NOs:29 and 30 are the nucleotide sequences of primers for amplification of the human collagen promoter.

DETAILED DESCRIPTION OF THE DISCLOSURE

The present disclosure provides molecules and methods for osteoblast-specific nuclear import or entry of DNA and robust osteoblast specific expression of a transgene. Nuclear import is mediated by polynucleotide sequences, designated "nuclear targeting sequences" or "nuclear entry sequences." The novel nuclear targeting sequences described herein offer the unique property of directing nuclear entry selectively in cells of the osteoblast lineage. This characteristic makes the osteoblast-specific nuclear targeting sequences described herein particularly suitable for delivering nucleic acids specifically to bone tissue, e.g., for diagnostic and therapeutic applications.

Thus, one aspect of the present disclosure relates to nucleic acids useful for introducing heterologous polynucleotide sequences into the nucleus of osteoblast lineage cells. In an embodiment, the disclosure provides an isolated or recombinant nucleic acid including an osteoblast-specific nuclear targeting sequence (alternatively referred to as a nuclear entry sequence). An exemplary osteoblast-specific nuclear targeting sequence is provided in SEQ ID NO:1, which represents position −267 through position +45 of a human alpha2(I) (pro)collagen gene (hCol1α2) promoter. Nucleotide positions are designated relative to the transcriptional start site (+1).

In certain embodiments, the nucleic acid includes an osteoblast-specific nuclear targeting sequence consisting essentially of SEQ ID NO:1. For example the osteoblast-specific nuclear targeting sequence can include at least a portion of SEQ ID NO:1 that retains nuclear targeting function. For example, the nucleic acid can include a portion (up to all) of SEQ ID NO:1 adjacent to or contiguous with sequences with which this portion of the hCol1α2 is not associated in the genomic form of the hCol1α2 gene. That is the portion of SEQ ID NO:1 can be flanked in the isolated or recombinant nucleic acid by heterologous polynucleotide sequences. In some embodiments, the portion of SEQ ID NO:1 is contiguous with a heterologous portion of the hCol1α2 gene (that is a portion of the hCol1α2 gene with which it is not associated in the human genome). In one embodiment, the nucleic acid includes at least a portion of SEQ ID NO:1 and no other sequences derived from the hCol1α2 gene.

Figure 1:
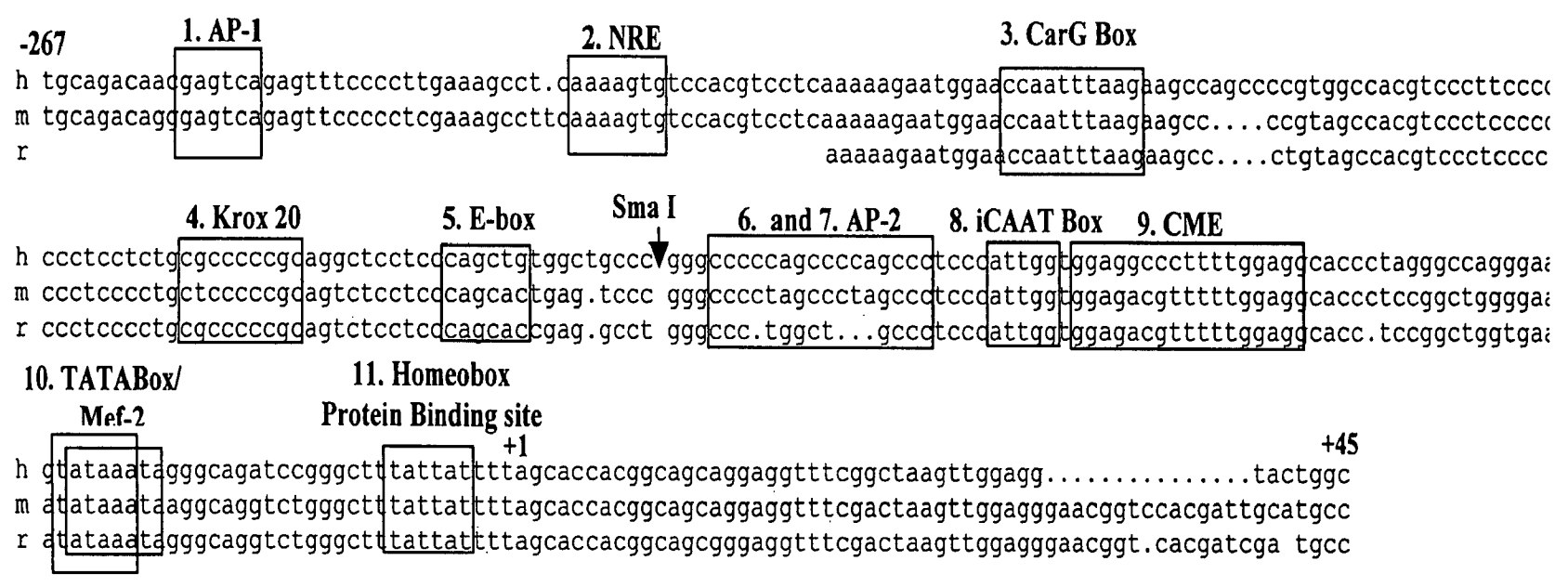

The isolated or recombinant nucleic acid can include an osteoblast-specific nuclear targeting sequence that is at least 95% identical to (such as at least 96%, or at least 97%, or even at least 98% or more than at least 99% identical to) at least a portion of the hCol1α2 promoter, such as the polynucleotide sequence represented by SEQ ID NO:1. For example, the osteoblast-specific nuclear targeting sequence can include one or a small number of nucleotide additions, deletions or substitutions while still maintaining nuclear entry function. Typically, any such additions, deletions or substitutions occur in a portion of the polynucleotide sequence that does not include a binding site for a nuclear DNA binding factor expressed in osteoblast lineage cells, e.g., as indicated in FIG. 1.

In general, following introduction of the nucleic acid into the cytoplasm of a cell, the osteoblast-specific nuclear targeting sequence directs entry of the nucleic acid into the nucleus of a non-dividing osteoblast lineage cell with an efficiency of at least 5%. For example, a nuclear transformation efficiency of at least about 10%, or at least about 20% distinguishes osteoblast-specific nuclear targeting activity with respect to undetectable nuclear transformation in the absence of an osteoblast nuclear targeting activity. Typically, the efficiency is much greater. For example, entry into the nucleus of non-dividing cells with an efficiency of greater than 40%, frequently greater than 50%, and often greater than about 60% or even 70% or higher is observed following introduction of the nucleic acid into the cytoplasm of non-dividing cell.

The nucleic acids described herein commonly include at least one additional polynucleotide sequence along with the osteoblast-specific nuclear targeting sequence. When present on the same nucleic acid molecule, the osteoblast-specific nuclear targeting sequence directs entry of the additional polynucleotide sequence into the nucleus of an osteoblast lineage cell. In some embodiments, the additional polynucleotide sequence is operably linked to the osteoblast-specific nuclear targeting sequence such that expression of the additional polynucleotide sequence is controlled by the polynucleotide including the osteoblast-specific nuclear targeting sequence. For example, the polynucleotide sequence including the osteoblast-specific nuclear targeting sequence can include a promoter, as well as additional sequences involved in efficient transcription of the operably linked sequence, such as a Kozak consensus sequence, or variant thereof. In addition, the nucleic acid can include one or more osteoblast-specific enhancers. The enhancer can be isolated from a gene other than hCol1α2. For example, the enhancer can be a portion of the hCbfa1/Runx2 gene (or a sequence with at least 95% sequence identity thereto, e.g., a sequence with at least 96%, 97%, 98% or 99% identity to a portion of the human hCbfa1/Runx2 transcription regulatory sequence). For example, the osteoblast-specific enhancer can be SEQ ID NO:2, SEQ ID NO:3; SEQ ID NO:4, or any combination thereof.

In some embodiments, the nucleic acid includes a first polynucleotide sequence including an osteoblast-specific nuclear targeting sequence and at least a second or additional polynucleotide sequence. Optionally, the additional polynucleotide sequence is operably linked to the osteoblast-specific nuclear targeting sequence such that the second polynucleotide sequence is expressed in at least one cell of the osteoblast lineage under the transcriptional control of the polynucleotide with the osteoblast-specific nuclear targeting sequence.

In some embodiments the additional or second polynucleotide sequence encodes a polypeptide, such as a protein, that exerts a beneficial or therapeutic effect when expressed in an osteoblast lineage cell. For example, nucleic acids can include a polynucleotide sequence that encodes an osteogenic factor, such as a fibroblast growth factor (e.g., FGF-1), insulin-like growth factor 1 or 2 (IGF-I), insulin-like growth factor binding proteins (IGFBP, e.g., IGFBP-5, IGFBP-6), a transforming growth factor beta (TGFβ), a vascular endothelial growth factor (VEGF), any one of a number of bone morphogenic proteins (BMPs), a cyclooxygenase (Cox1, Cox2), a LIM mineralization protein (LMP), a helix-loop-helix protein (e.g., Twist, Id1, Id3), a Runt-related transcription factor 2 (Runx2, also called Cbfa1)) or an osterix transcription factor operably linked to a polynucleotide sequence including an osteoblast-specific nuclear targeting sequence. Nucleic acids including such osteogenic polypeptides operably linked to a polynucleotide sequence with an osteoblast-specific nuclear targeting sequence can be introduced and expressed specifically in osteoblast lineage cells using the methods described herein. In an embodiment, the nucleic acid includes a polynucleotide encoding a type I alpha (1 or 2) procollagen polypeptide. Such a nucleic acid can be introduced into a subject using the methods described herein, for example, to treat osteogenesis imperfecta. In another embodiment, the nucleic acid includes a polynucleotide sequence encoding a calcitonin polypeptide. Such a nucleic acid can be introduced, e.g., to treat or prevent osteoporosis. In another embodiment, the nucleic acid includes a polynucleotide sequence encoding cyclooxygenase-2. Such a nucleic acid can be introduced, e.g., to treat and accelerate fracture repair. In some embodiments, the polypeptide is a polypeptide that inhibits or interferes with a protein expressed in osteoblast lineage cells. Such polypeptides include dominant negative forms of proteins, binding proteins (such as antibodies and antibody fragments, soluble receptors), fusion proteins, etc., that interfere with expression or inhibit the activity of proteins, such as IGFBP-6, TWIST, IL-18 and IL-17B receptor that increase bone loss.

In other embodiments, the nucleic acid includes a polynucleotide sequence that encodes a functional RNA molecule, such as an antisense RNA, an siRNA, or a ribozyme that diminishes, interferes with or modifies expression of an RNA or protein expressed in osteoblast lineage cells. For example, the nucleic acid can include an siRNA (or other inhibitory RNA molecule) that interferes with, and decreases expression of, a factor that increases bone loss (such as, TWIST, IL-18, IGFBP-6). Similarly, inhibitory RNAs specific for the interleukin-1 receptor (IL-1R) and/or for Receptor Activator of NF-κB Ligand (RANKL) or IGFBP-6 can be introduced and expressed in osteoblast lineage cells using the methods described herein to treat osteoporosis. Nucleic acids including a polynucleotide sequence that encodes an inhibitory RNA molecule operably linked to a polynucleotide sequence with an osteoblast-specific nuclear targeting sequence can also be used to treat conditions that result in abnormal overgrowth of bone, such as post-amputation hyperplasia and hereditary hyperostosis syndromes. Favorable targets for interference by siRNA include, for example, osteocalcin, procollagen, cyclooxygenase 2, LMP, BMP, VEGF, FGF, IGF, and IGFBP genes.

In some cases the nucleic acid including the osteoblast-specific nuclear targeting sequence (for example, and a polynucleotide encoding a polypeptide or functional RNA of interest) is incorporated in a vector. For example, the vector can be a plasmid. Alternatively, the vector can be a viral vector (e.g., a retroviral vector, an adenoviral vector, an adeno-associated viral (AAV) vector or a lentiviral vector), or a linear double stranded nucleic acid.

Host cells incorporating the above-described nucleic acids are also a feature of the disclosure.

Another aspect of the present disclosure relates to methods for introducing a nucleic acid (e.g., a heterologous nucleic acid) into the nucleus of an osteoblast lineage cell. The methods involve introducing a nucleic acid with an osteoblast-specific nuclear targeting sequence into at least one osteoblast lineage cell. Following introduction into the cell using well-known molecular biology techniques, such as lipid mediated transformation microinjection, electroporation, and particle-bombardment (biolistic), the DNA enters the nucleus under the direction of the osteoblast-specific nuclear targeting sequence. In some embodiments, the nucleic acid includes an additional polynucleotide sequence that is operably linked to the polynucleotide sequence with the osteoblast-specific nuclear targeting sequence. In this case, the additional polynucleotide sequence is introduced into the nucleus of the osteoblast-lineage cell along with the osteoblast-specific nuclear targeting sequence. Such additional polynucleotide sequences can, for example, encode polypeptides or functional RNA molecules, the expression of which is desired in the osteoblast lineage cell. In general, the osteoblast-specific nuclear targeting sequence directs entry of the nucleic acid into the nucleus at an efficiency of at least about 5% in non-dividing cells. For example, a entry of the nucleic acid into the nucleus at an efficiency of at least about 10%, or at least about 20% distinguishes osteoblast-specific nuclear targeting activity with respect to undetectable nuclear transformation in the absence of an osteoblast nuclear targeting activity. Typically, the efficiency is much greater. For example, entry into the nucleus of non-dividing cells with an efficiency of greater than 40%, frequently greater than 50%, and often greater than about 60% or even 70% or higher is observed following introduction of the nucleic acid into the cytoplasm of non-dividing cell.

The present disclosure also relates to methods for expressing heterologous polynucleotide sequences in osteoblast lineage cells. A method for expressing a heterologous polynucleotide in an osteoblast lineage cell involves introducing a nucleic acid including a heterologous polynucleotide sequence operably linked to an osteoblast-specific nuclear targeting sequence. Following introduction of the nucleic acid into the cell, the cell is maintained under conditions in which the heterologous polynucleotide is expressed. In some embodiments the osteoblast-specific nuclear targeting sequence is sufficient to produce a desired level of expression.

In some cases, an additional polynucleotide sequence that includes an enhancer is incorporated into the nucleic acid. The enhancer is selected for its activity in osteoblast lineage cells. For example, to produce robust (strong) expression, the heterologous nucleic acid can be operably linked to a polynucleotide sequence including an osteoblast-specific nuclear targeting sequence (such as the hCol1α2 promoter sequence described above) and a strong osteoblast-specific enhancer, such as an enhancer isolated from the hCbfa1/Runx2 gene (e.g., SEQ ID NO:2, SEQ ID NO:3 and/or SEQ ID NO:4). The nucleic acid including the heterologous polynucleotide sequence operably linked to the chimeric transcription/nuclear targeting sequence is then introduced into a host cell where it is expressed following entry into the nucleus. As will be appreciated by one of ordinary skill in the art, the heterologous polynucleotide sequence can encode a polypeptide (for example, a cellular protein expressed in an osteoblast lineage cell). Exemplary polypeptides useful in a therapeutic context are described above, e.g., FGFs, IGF-1, IGF-2, TGFβ, VEGF, BMPs, LMPs, cyclooxygenase-2, IGFBPs, Cbfa1/Runx2, osterix, IL-17B, type I alpha (1 or 2) procollagen, calcitonin, osteonectin, osteopontin, etc. Likewise, polypeptides that interact with or bind to such cellular polypeptides can be encoded by the heterologous polynucleotide sequence. Similarly, the heterologous polynucleotide sequence can encode a functional RNA molecule, e.g., an siRNA, antisense RNA or ribozyme, that inhibits or modulates expression of a gene expressed in osteoblast lineage cells.

The cells into which a nucleic acid including an osteoblast-specific nuclear targeting sequence are introduced can be in vitro, such as cells removed from the bone marrow of a subject and placed in culture medium (optionally in the presence of growth and other factors suitable for the induction of osteogenic differentiation). Cells in vitro also include established osteoblast lineage cell lines (such as hFOB cells, C2C12 cells, 7F2 cells, ROS 17/2.8 cells, SaOS-2 cells, TE-85 cells, MG-63 cells, U-2 OS cells and MC3T3-E1 cells) into which a nucleic acid has been introduced according to the methods described herein. Alternatively, the cells are in vivo, for example in a subject to be treated (therapeutically or prophylactically) for a bone related disorder (such as, osteoporosis, fracture, osteopetrosis, osteogenesis imperfecta, bone loss associated with aging and/or immobility, post-amputation hyperplasia, hyperostosis, or other conditions affecting normal bone metabolism). The cells are typically mammalian cells, such as human cells. Such cells, and the RNAs and/or polypeptides they produce, are features of this disclosure.

The disclosure also provides methods for identifying agents that produce an effect on an osteoblast lineage cell. The methods can be utilized to identify agents that exert an effect on a cell with the normal physiological characteristics of an osteoblast lineage cell, as well as to identify agents that exert an effect on a cell with genetic, physiological and/or phenotypic characteristics of an osteoblast lineage cell in a pathological condition, such as osteogenesis imperfecta, osteoporosis, osteoarthritis, fracture, amputation, osteopetrosis, hyperostosis, cancer (e.g., osteosarcoma and cancers with ectopic expression of transcription factors that initiate osteoblast-specific nuclear entry, such as, prostate and breast cancers that express Runx2), etc. Such methods involve contacting a cell, generally an osteoblast lineage cell (such as an established cell from an osteoblast linage cell line) that includes a nucleic acid with a osteoblast-specific nuclear targeting sequence with at least one test agent and detecting an effect on the cell. In some embodiments, the cell includes a nucleic acid with a reporter operably linked to the osteoblast-specific nuclear targeting sequence. In certain embodiments, the cell includes a nucleic acid with a polypeptide or RNA that induces a physiological condition that mimics a disorder of bone metabolism (that is, provides a transgenic model of a disorder of bone metabolism in a cell or organism.

The test agent can be a member of a composition or compound library, such a library can include without limitation natural products, chemical compositions, biochemical compositions, polypeptides, peptides, antibodies, nucleic acids, antisense RNAs, iRNAs, siRNAs, dsRNAs, ribozymes, etc. The detected effect on the cell can be a genetic effect (e.g., detected as a difference in transcription of one or more target genes, such as by hybridization to a microarray, or by a difference in expression of a reporter gene), a physiological effect (e.g., detected by measuring production of proteins involved in of bone metabolism, such as osteopontin, osteonectin, osteocalcin, bone sialoprotein, alkaline phosphatase, and type I collagen, for example using a radioimmunoassay or ELISA), or a phenotypic effect (e.g., by detecting morphological characteristics typical of osteoblast lineage cells).

The disclosure also provides kits and reagents useful in the methods described herein. The kits typically include one or more nucleic acids as described herein, along with various control nucleic acids, buffers, detection reagents, and/or cells. Commonly, such a kit also includes directions for the use of kit components. Typically, a kit is packaged in one (or more than one related) packaging material for convenient handling, shipping and/or storage.

Additional details regarding specific embodiments of the disclosure are provided below.

DEFINITIONS

Unless otherwise explained, all technical and scientific terms used herein have the same meaning as commonly understood by one of ordinary skill in the art to which this disclosure belongs. Definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

In order to facilitate review of the various embodiments of this disclosure, the following explanations of specific terms are provided:

The term "nuclear targeting sequence" or "nuclear entry sequence" refers to a nucleic acid sequence that is sufficient to mediate uptake of a nucleic acid by the nucleus, following introduction of the nucleic acid into a cell.

The term "cell-specific" in reference to a nuclear targeting sequence indicates that the nuclear targeting sequence mediates incorporation of a nucleic acid into the nuclei of a specific cell type (or types) and does not facilitate uptake of the nucleic acid into the nuclei of other cell types. "Specific cell type" refers to a type of cell (for example, osteoblasts), or to more than one cell type within a specific class of cells, for example osteoblast lineage cells. Thus, an "osteoblast-specific nuclear targeting sequence" mediates introduction of a nucleic acid containing such a sequence into the nucleus of an osteoblast lineage cell but not into the nuclei of other cell types, such as fibroblasts. Specificity for a particular cell type or lineage, such as osteoblast lineage cells, is achieved when the specified cell type is discriminated/achieved in at least 98% of trials.

The term "osteoblast" includes bone progenitor cells which have the capacity to form, or to contribute to the formation of, new bone tissue. Osteoblasts include osteocytes and more immature osteoblast lineage cells. The term "cell lineage" refers to the ancestry (i.e., the progenitor cell and program of cell divisions) of a cell. Thus, an "osteoblast lineage cell" is any cell that arises by division of a committed osteoblast progenitor, such as a preosteoblast, osteoblast or osteocyte.

The phrase "nuclear DNA binding proteins" or "nuclear DNA binding polypeptides" refers to DNA binding proteins that reside in the nucleus. These nuclear DNA binding proteins are characterized by the ability to bind to short DNA sequences with sequence specificity. Typically, such nuclear DNA binding proteins are transported into the nucleus of a cell because they contain a nuclear localization sequence (NLS) or because they complex with one or more other proteins that contain an NLS. Nuclear DNA binding proteins have various functions in the regulation of DNA transcription and/or replication. Nuclear DNA binding proteins include, for example, transcription factors, DNA replication factors, and telomere or centromere binding proteins. For a general discussion of nuclear, DNA binding proteins, see, e.g., Nigg Nature 386:779 [1997].

A "transcription factor" or "TF" is a protein that promotes RNA polymerase recognition and/or initiation and/or activation and/or repression of expression of a polynucleotide sequence. The binding of an RNA polymerase to a promoter is important for the initiation of transcription of a polynucleotide sequence. Transcription is the process by which a nucleic acid template, e.g., DNA, is copied into a single stranded RNA molecule (which can in some cases assume a double stranded configuration based on sequence composition). In some cases the transcribed RNA molecule (e.g., an mRNA) is translated into a protein.

The term "gene" refers to a functional nucleic acid (e.g., DNA or RNA) sequence. A gene can include coding sequences necessary for the production of a functional RNA or polypeptide (e.g., a protein of interest). The polypeptide can be encoded by a full length coding sequence or by any portion of the coding sequence so long as the desired activity or functional properties (e.g., enzymatic activity, ligand binding, signal transduction, etc.) of the full-length polypeptide, or fragment, are retained. The term also encompasses sequences associated with (e.g., contiguous with or adjacent to) a coding region that are involved in regulation of expression of the coding sequence, such as 5' untranslated sequences including for example, a promoter, enhancers and other sequences which serve as the recognition sites for protein factors involved in expression of the polynucleotide sequence. The term gene encompasses both cDNA (complementary DNA) and genomic forms of a gene.

A "transgene" is a heterologous nucleic acid, e.g., a heterologous "gene" introduced into a recipient cell or organism. Such a recipient cell, into which a heterologous nucleic acid has been introduced is referred to as a "host" cell.

The terms "transfection," "transduction" and "transformation" refer to the introduction of heterologous DNA/RNA into cells. These terms are used interchangeably to refer to the introduction of nucleic acids into host cells regardless of the methodology used. Common methods for introducing nucleic acids into cells include calcium phosphate-DNA co-precipitation, DEAE-dextran-mediated transfection, polybrene-mediated transfection, electroporation, microinjection, liposome fusion, lipofection, protoplast fusion, retroviral or adenoviral infection, and biolistics.

The term "nucleic acid" refers to a polymer of nucleotides of any length. The term includes single- and double-stranded forms of DNA (deoxyribonucleic acid) and RNA (ribonucleic acid), as well as DNA-RNA hybrids. Generally, the term "nucleic acid" is synonymous with "polynucleotide" or "polynucleotide sequence," unless clearly indicated to the contrary. The repeating units in DNA (RNA) polymers are four different nucleotides, each of which comprises one of the four bases, adenine, guanine, cytosine and thymine (uracyl) bound to a deoxyribose (ribose) sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed. Unless otherwise specified, any reference to a DNA molecule is intended to include the reverse complement of that DNA molecule. Double-stranded DNA and RNA (dsDNA and dsRNA) have two strands, which can be defined with respect to the products that they encode: a 5'→3' strand, referred to as the plus or "sense" strand, and a 3'→5' strand (the reverse compliment), referred to as the minus or "antisense" strand. Because RNA polymerase adds nucleic acids in a 5'→3' direction, the minus strand of the DNA serves as the template for the RNA during transcription. Thus, the RNA formed will have a sequence complementary to the minus strand and identical to the plus strand (except that U is substituted for T). Except where single strandedness is required by context, DNA molecules, although written to depict only a single strand, encompass both strands of a double-stranded DNA molecule.

For convenience, short polynucleotides, typically of less than about 100 nucleotides in length are often referred to as "oligonucleotides." Similarly, very short polymers of two, three, four, five, or up to about 10 nucleotides in length, can conveniently be referred to as dinucleotides, trinucleotides, tetranucleotides, pentanucleotides, etc. The nucleotides can be ribonucleotides, deoxyribonucleotides, or modified forms of either nucleotide.

A "recombinant" polynucleotide includes a polynucleotide that is not immediately contiguous with one or both of the polynucleotide sequences with which it is immediately contiguous (one on the 5' end and one on the 3' end) in the naturally occurring genome of the organism from which it is derived. Thus, a recombinant nucleic acid can include polynucleotide sequences that are "heterologous" with respect to each other. A "heterologous" polynucleotide is a polynucleotide that is not normally (e.g., in the wild-type genomic sequence) found adjacent to a second polynucleotide sequence, or that is not normally found within a particular cell, as the reference indicates. A heterologous nucleic acid or a heterologous polynucleotide can be, but is not necessarily, transcribable and translatable. In some embodiments, a heterologous nucleic acid is a cDNA or a synthetic DNA. In other embodiments, the heterologous polynucleotide sequence is a genomic sequence that encodes an RNA transcript. In other embodiments, a heterologous polynucleotide encodes a reporter. Similarly, a recombinant protein is a protein encoded by a recombinant nucleic acid molecule. A recombinant protein can be obtained by introducing a recombinant nucleic acid molecule into a host cell (such as a eukaryotic cell or cell line, such as a mammalian cell or yeast, or a prokaryotic cell, such as bacteria) and causing the host cell to produce the gene product. Methods of causing a host cell to express a recombinant protein are well known in the art (see, e.g., Sambrook et al., *Molecular Cloning. A Laboratory Manual,* 2nd edition, New York: Cold Spring Harbor Laboratory Press, 1989).

An "isolated" biological component (such as a polynucleotide, polypeptide, or cell) has been purified away from other biological components in a mixed sample (such as a cell or nuclear extract). For example, an "isolated" polypeptide or polynucleotide is a polypeptide or polynucleotide that has been separated from the other components of a cell in which the polypeptide or polynucleotide was present (such as an expression host cell for a recombinant polypeptide or polynucleotide).

The term "purified" refers to the removal of one or more extraneous components from a sample. For example, where recombinant polypeptides are expressed in host cells, the polypeptides are purified by, for example, the removal of host cell proteins thereby increasing the percent of recombinant polypeptides in the sample. Similarly, where a recombinant polynucleotide is present in host cells, the polynucleotide is purified by, for example, the removal of host cell polynucleotides thereby increasing the percent of recombinant polynucleotide in the sample. Isolated polypeptides or nucleic acid molecules, typically, comprise at least 50%, at least 60%, at least 70%, at least 80%, at least 90%, at least 95% or even over 99% (w/w or w/v) of a sample.

Polypeptides and nucleic acid molecules are isolated by methods commonly known in the art and as described herein. Purity of polypeptides or nucleic acid molecules can be determined by a number of well-known methods, such as polyacrylamide gel electrophoresis for polypeptides, or agarose gel electrophoresis for nucleic acid molecules.

A "promoter" is a polynucleotide sequence sufficient to direct transcription of a nucleic acid. Typically, a promoter is situated adjacent (although not necessarily contiguous) to the start site of transcription. A promoter includes, at a minimum, a polynucleotide sequence to which an RNA polymerase can bind and initiate transcription of an operably linked polynucleotide ("minimal promoter"). A polynucleotide including a promoter can also include elements that restrict promoter-dependent expression to selected cells or tissues, or that render expression inducible by external signals or agents; such elements can be located in the 5' or 3'regions of the gene. Both constitutive and inducible promoters have been described (see e.g., Bitter et al., *Meth. Enzymol.,* 153:516-544, 1987). Specific, non-limiting examples of promoters include promoters derived from the genome of mammalian cells (e.g., metallothionein promoter) and from mammalian viruses (e.g., cytomegalovirus (CMV) immediate early gene; Rous Sarcoma virus (RSV) long terminal repeat; the adenovirus late promoter; the vaccinia virus 7.5K promoter), as well as from bacteriophage, plants and plant viruses. Promoters can also be produced by recombinant DNA or synthetic techniques.

A first polynucleotide sequence is "operably linked" to a second polynucleotide sequence when the first polynucleotide is in a functional relationship with the second polynucleotide. For instance, a coding sequence is operably linked to a transcription control sequence if the transcription control sequence affects (e.g., regulates or controls) the transcription or expression of the coding sequence. When recombinantly produced, operably linked polynucleotides are usually contiguous and, where necessary to join two protein-coding regions, are in the same reading frame. However, polynucleotides need not be contiguous to be operably linked.

"Expression" refers to transcription of a polynucleotide, and when used in reference to a polypeptide, to translation. Expression is the process by which the information encoded by polynucleotide sequence is converted into an operational, non-operational or structural component of a cell. The level or amount of expression is influenced by cis-acting elements and trans-acting binding factors, which are often subject to the influence of intra- and/or extra-cellular stimuli and signals. The response of a biological system, such as a cell, to a stimulus can include modulation of the expression of one or more polynucleotide sequences. Such modulation can include increased or decreased expression as compared to pre-stimulus levels. Expression can be regulated or modulated anywhere in the pathway from DNA to RNA to protein (and can include post-translations modifications, e.g., that increase or decrease stability of a protein). For example, the cellular response to a stimulus that promotes differentiation of a stem cell into a committed osteoblast lineage cell, includes induction of expression of cell type specific genes, such as Runx2 and osterix. It should be noted that different biological systems can respond differently to an identical stimulus.

A polynucleotide sequence is said to "encode" a polynucleotide or polypeptide if the information contained in the nucleotide sequence can be converted structurally or functionally into another form. For example, a DNA molecule is said to encode an RNA molecule, such as a messenger RNA (mRNA) or a functional RNA (such as an inhibitory RNA (iRNA), small inhibitory RNA (siRNA), double stranded RNA (dsRNA), small modulatory RNA (smRNA), antisense RNA (asRNA) or ribozyme, if the RNA molecule is transcribed from the DNA molecule, and contains at least a portion of the information content inherent in the DNA molecule. A DNA or RNA molecule is said to encode a polypeptide, e.g., a protein, if the protein is translated on the basis of a sequence of trinucleotide codons included within the DNA or RNA molecule. Where the coding molecule is a DNA, the polypeptide is typically translated from an RNA intermediary corresponding in sequence to the DNA molecule.

The term "polypeptide" refers to any chain of amino acids, regardless of length or post-translational modification (for example, glycosylation or phosphorylation), such as a protein or a fragment or subsequence of a protein. The term "peptide" is typically used to refer to a chain of amino acids of from about 3 to about 30 amino acids in length. For example an immunologically relevant peptide can be from about 7 to about 25 amino acids in length, e.g., from about 8 to about 10 amino acids.

A "vector" is a nucleic acid as introduced into a host cell, thereby producing a transformed host cell. Exemplary vectors include plasmids, cosmids, phage, animal and plant viruses, artificial chromosomes, and the like. Vectors also include naked nucleic acids, liposomes, and various nucleic acid conjugates. Certain vectors are capable of autonomous replication in a host cell into which they are introduced (for example, vectors having a bacterial origin of replication replicate in bacteria hosts). Other vectors can be integrated into the genome of a host cell upon introduction into the host cell and are replicated along with the host genome. Some vectors contain expression control sequences (such as, promoters) and are capable of directing the transcription of an expressible nucleic acid sequence that has been introduced into the vector. Such vectors are referred to as "expression vectors." A vector can also include one or more selectable marker genes and/or genetic elements known in the art.

A "reporter" is a molecule that serves as an indicator of a biological activity. In the context of the present disclosure, a reporter serves as an indicator of transcriptional activity unless otherwise indicated. Typically, a reporter is selected for ease of detection, e.g., by optical means. Common reporters include fluorescent proteins, such as green fluorescent protein (GFP) and numerous variants thereof. Other reporters include proteins with enzymatic activities that convert a fluorogenic or chromogenic substrate into a fluorescent or visible product, or that convert an isotopically labeled substrate into a radioactive product. Examples of such enzymatic reporters include firefly luciferase, chloramphenicol acetyltransferase (CAT), β-glucuronidase and β-galactosidase. A polynucleotide encoding a reporter can be operably linked to a transcription control sequence and introduced into cells. If the transcription control sequence is active in the cell, the reporter will be expressed, and its activity can be detected (qualitatively or quantitatively) using techniques known in the art. Reporters also include selectable markers, the activity of which can be measured as relative resistance or sensitivity to a selection agent, such as an antibiotic.

A "test compound" refers to any chemical entity (element, compound, molecule, complex), to be evaluated for its potential effect (genetic, physiologic and/or phenotypic) on a cell or organism. In some cases test compounds are pharmaceutical compositions, e.g., drugs, and the like that can be used to treat, mitigate, alleviate or prevent a disease, illness, sickness, or disorder of bodily function, or otherwise alter the physiological or cellular status of an organism. Test compound also includes those chemical entities, pharmaceuticals, drugs, which act to enhance or improve an otherwise normal or nominal physiological or cellular function or status. Test compounds comprise both known and potential therapeutic compounds. A test compound can be determined to be therapeutic by using the present disclosure in the screening methods to discover molecules that affect an activity of a specific cell type, for example, an osteoblast. A "known therapeutic compound" refers to a therapeutic compound that has been shown (e.g., through animal trials or prior experience with administration to humans) to be effective in such treatment or prevention.

In the context of the present disclosure, a "library," for example a composition library, a compound library or a library of agents or potential agents, is a collection of compositions, compounds, agents, etc. A library can be restricted to a single class of compounds or can include a variety of differently classified compounds or compositions. A library can be organized and stored as a single collection or dispersed in multiple locations. A "member of a library" or "library member" is a component of such a collection. Libraries can include, without limitation, inorganic compounds, organic compounds (e.g., produced by combinatorial synthesis), natural products, chemical compositions, biochemical compositions (such as nucleic acids, e.g., DNA, RNA, DNA-RNA hybrids, antisense RNAs, dsRNAs, iRNAs, siRNAs, smRNAs and ribozymes, and peptides, polypeptides, fusion polypeptides, proteins, e.g., antibodies, and the like), metabolites, etc.

As used herein, the term "response," when used in reference to an assay, refers to the generation of a detectable signal (e.g., accumulation of reporter protein, or accumulation of a detectable product).

"siRNAs" are small interfering RNAs. siRNAs can comprise a duplex, or double-stranded region, of about 18-25 nucleotides long; or siRNAs can contain from about two to four unpaired nucleotides at the 3' end of each strand. At least one strand of the duplex or double-stranded region of a siRNA is substantially homologous to, or substantially complementary to, a target RNA molecule. The strand complementary to a target RNA molecule is the "antisense strand;" the strand homologous to the target RNA molecule is the "sense strand," and is also complementary to the siRNA antisense strand. siRNAs can also contain additional sequences; non-limiting examples of such sequences include linking sequences, or loops, as well as a stem loop and other folded structures. siRNAs appear to function as key intermediaries in triggering RNA interference in invertebrates and in vertebrates, and in triggering sequence-specific RNA degradation during post-transcriptional gene silencing in plants. "RNA interference" or "RNAi" refers to the silencing or decreasing of gene expression by siRNAs. In particular, RNA interference is sequence-specific, post-transcriptional gene silencing in animals and plants, initiated by siRNA which is homologous in its duplex region to the sequence of the silenced gene. The gene can be endogenous or exogenous to the organism, present integrated into a chromosome or present in a transfection vector that is not integrated into the genome. The expression of the gene is either completely or partially inhibited. RNAi can also be considered to inhibit the function of a target RNA.

Nucleic Acids Comprising an Osteoblast-specific Nuclear Targeting Sequence

The present disclosure relates to nucleic acids that include a polynucleotide sequence that contains binding sites for a set of osteoblast specific nuclear DNA binding proteins. These polynucleotide sequences, referred to as "osteoblast-specific targeting sequences" or "osteoblast-specific nuclear entry sequences" specifically direct entry of the nucleic acids that contain them into the nucleus of osteoblast lineage, but not to the nuclei of other cells. Thus, the osteoblast-specific targeting sequences, and nucleic acids (or constructs) described herein are particularly useful for selectively targeting a nucleic acid of interest to the nucleus of osteoblast lineage cells. The following detailed description relates to an osteoblast-specific nuclear targeting sequence isolated from the promoter region of the human alpha 2 type I procollagen gene (hCol1α2). However, additional osteoblast-specific nuclear targeting sequences including multiple binding sites for osteoblast specific DNA binding factors can be identified, for example using a variety of computer assisted genetic search algorithms (genomic algorithms), and their activity confirmed according to the methods described herein.

Exemplary nuclear targeting sequences have been described previously in U.S. Pat. Nos. 5,827,705 and 6,130,207, the disclosures of which are incorporated herein for all purposes.

Without being limited by theory, it is likely that the mechanism of nuclear entry involves the interaction of nuclear DNA binding protein, such as transcription factors (TFs) containing nuclear localization signals (NLSs) with pDNA sequences containing the osteoblast-specific nuclear targeting sequence. General and/or osteoblast specific transcription factors involved in targeting DNA into the osteoblast nucleus bind to the pDNA. The NLSs then bind to the nuclear import machinery (importin alpha/beta) which moves the DNA/protein complex through the nuclear pore complex (NPC) into the nucleus. Nuclear DNA binding proteins capable of interacting with osteoblast-specific nuclear targeting sequences include transcription factors, co-activators, co-repressors, enzymes and steroid hormone receptors expressed in osteoblast lineage cells. Nucleic acids, lacking the osteoblast-specific nuclear targeting sequence are not bound by the nuclear DNA binding factors expressed in osteoblast cells that promote nuclear import, and cannot be transported through the NPC by the nuclear import machinery.

A plasmid including a nuclear targeting sequence, e.g., from a human collagen gene promoter (hCol1α2) binds NLS-containing TFs that are produced specifically in osteoblasts and mediate nuclear import. Since the required combination of osteoblast specific TFs is not formed in other cell types (such as fibroblasts and chondrocytes), nuclear import of the hCol1α2 promoter plasmid does not occur in these cells. Optionally, the plasmid can include sequences that increase transcription of an operably linked polynucleotide resulting robust expression.

FIG. 1 shows the structure of the type I alpha 2 procollagen proximal promoter regions, and compares the Col1a2 promoters from multiple species (human, rat and mouse) illustrating conserved control elements that bind to transcription factors involved in mediating nuclear entry in osteoblasts. Base pair sequence numbers −267 to +45 (relative to the transcription start site) are provided for the human promoter sequence. Each of the binding sites within the proximal regulatory region (designated by numbered boxes) is important for osteoblast specific basal promoter activity and nuclear entry. Basal activity and nuclear entry activity is lost when the sequences from −267 to −108 region (using the Sma I restriction site) are removed. Nuclear entry activity is also lost when any one of the eleven regulatory regions is mutated. The following regulatory elements are shown as numbered boxes in FIG. 3: 1. AP-1=Activator Protein-1 (Jun and Fos family members); 2. NRE=Nkx 3.2 response element; 3. CArG Box, serum response element; 4. Krox 20, Egr-1 binding site; 5. E-box, basic helix-loop-helix binding site; 6. and 7. Dual AP-2 sites, Activator protein-2 binding site; 8. iCAAT Box=inverted CAAT Box; 9. CME=collagen modulating element; 10. Mef-2, myocyte enhancer factor; and 11. homeodomain binding site. Mutation of any one of the eleven regulatory elements results in loss of nuclear entry activity, whereas the effect of mutation on basal promoter activity is variable.

The relative position and order of these DNA binding sites (regulatory elements) can also be important in conferring nuclear entry specificity because other promoters expressed in osteoblasts with many of the same DNA regulatory elements do not transport DNA into the osteoblast nucleus. Table 1 shows that while many known osteoblast promoters have varying degrees of commonality in transcription factor binding sites or regulatory elements to drive expression specifically in osteoblasts, osteoblast nuclear entry activity is not observed for the promoters of all genes expressed in osteoblasts.

In accordance with the present disclosure, a nucleic acid, such as a plasmid vector, a viral vector, or a linear DNA molecule (e.g., created by digestion of a plasmid with restriction enzymes or by PCR), can be constructed for cell-specific import into the nuclei of osteoblasts (or other osteoblast lineage cells) using a polynucleotide sequence with an osteoblast-specific nuclear targeting sequence, such as a polynucleotide sequence from the promoter region of the hCol1α2 gene. The polynucleotide sequence from −267 to +45 of the hCol1α2 proximal promoter is represented by SEQ ID NO:1. The polynucleotide sequence of SEQ ID NO:1 can be an isolated nucleic acid molecule, or can be incorporated in a vector construct such as a plasmid, a viral vector or a linear DNA molecule The nucleic acid sequences referred to herein (SEQ ID NOs:1-4) are defined to include, but not require, the complementary nucleic acid strand. SEQ ID NOs:1-4 are further defined to include, in addition to the foregoing, the inverse sequence, i.e., wherein the normal reading frame is reversed. Complementary sequences are those that are capable of base pairing according to the standard Watson-Crick rules.

In one embodiment, the cell-specific nuclear targeting molecule can have a nucleic acid sequence as shown in SEQ ID NO:1. SEQ ID NO:1 is the 267 base pairs of the 5'-flanking sequence immediately upstream (5' to) the transcription start site and the first 45 base pairs of the 5' untranslated region of the first exon of the hCol1α2 gene). Truncated versions of the hCol1α2 lacking nucleotides from position −267 to position −108 have no nuclear entry activity. The entire sequence of the hCol1α2 gene with nuclear entry activity is provided, e.g., in GENBANK®, Accession Nos. NM_000089. SEQ ID NO:1 corresponds to nucleotide positions 68-379 of NM_000089.

Figure 3:
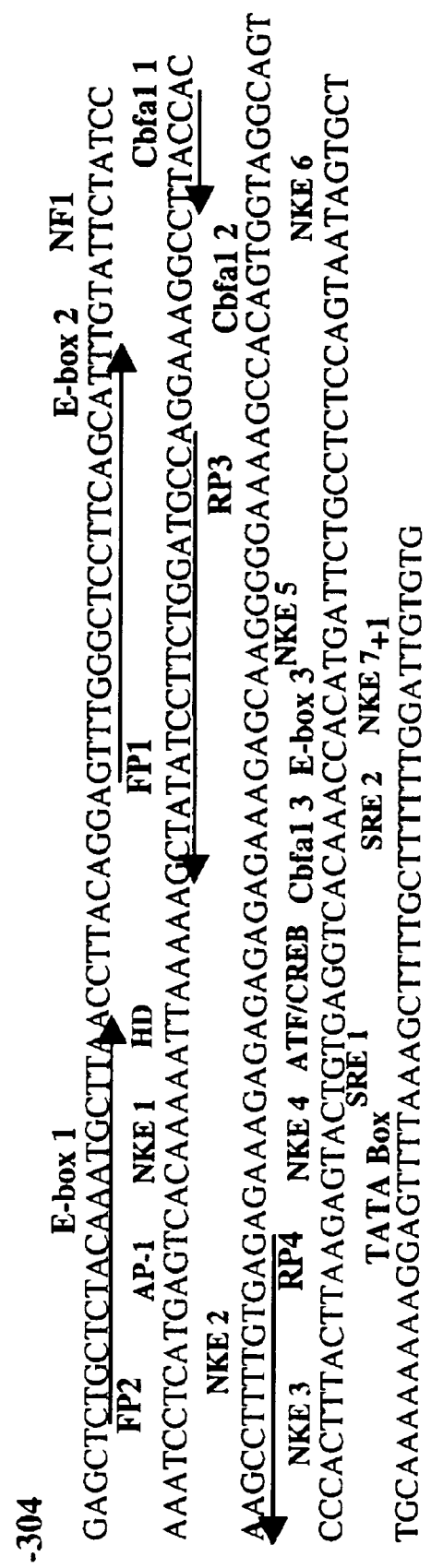
FIG. 3 is a representation of the DNA sequence of the osteoblast specific enhancer within the proximal hCbfa1/Runx2 promoter.

When constructing plasmid, viral or linear DNA molecules for expressing polynucleotide sequences (e.g., transgenes) in a eucaryotic host cell, enhancer sequences can be inserted into the DNA sequences to increase transcriptional efficiency. Enhancer sequences are eucaryotic DNA regulatory elements that increase transcriptional efficiency in a manner relatively independent of their position and orientation with respect to a nearby gene. Enhancer sequences have the remarkable ability to function upstream from, within, or downstream from transgenes. Numerous enhancer elements are known in the art, including the enhancer from the CMV (cytomegelovirus) immediate early promoter or the retroviral long terminal repeats of LTRs, as well as numerous tissue and/or lineage specific mammalian enhancers. In some embodiments, nucleic acid enhancer sequences isolated or derived from the hCbfa1/Runx2 gene, (represented as SEQ ID NOs:2-4) are utilized. These enhancer sequences are shown in FIG. 3. Referring to FIG. 3, putative regulatory elements are indicated in the DNA sequence. An osteoblast specific enhancer element resides between the FP1 and RP3 primers. The NF1 site is split and overlaps with E-Box 2. The three Cbfa1 binding sites are indicated and inhibit basal promoter activity. In FIG. 3, the following regulatory elements are indicated: AP-1=activator protein 1; C/EBP=CAAT Enhancer Binding protein; and ATF/CREB, cAMP response element binding protein. The human Cbfa1/Runx2 promoter sequence is found, e.g., in GENBANK® Accession No. AB013356.

SEQ ID NO:1 is sufficient for nuclear entry. In some embodiments, SEQ ID NO:1 is used both for nuclear entry and to direct transgene expression. In other embodiments, the hCol1 a2 nuclear entry/promoter sequence can be used, in combination with the specific enhancer sequences (SEQ ID NOs:2-4) to direct nuclear entry and/or for strong transgene expression in the osteoblast. Accordingly, the nucleic acids (e.g., vectors) described herein include SEQ ID NO:1, alone, or with an enhancer DNA sequence to increase expression in osteoblasts. Nuclear import of these vectors or linear DNA containing the hCol1α2 nuclear entry/promoter (e.g., SEQ ID NO:1) occurs only in osteoblasts and no other cell type, including fibroblasts and chondrocytes. Based on these findings, a new generation of DNA expression molecules (for example plasmid vectors, viral vectors and linear DNA molecules) that target gene delivery specifically to osteoblasts have been created by identifying and duplicating sequences in a promoter (expressed in osteoblasts) that have intrinsic osteoblast specific nuclear entry activity. For example, FIG. 2 illustrates an exemplary plasmid vector including an hCol1α2 nuclear entry/promoter sequence that is capable of mediating movement of nucleic acids into the osteoblast nucleus. As illustrated in FIG. 2, the hCol1α2 nuclear entry/promoter sequence replaces the CMV promoter in the pCMV-GFP vector (Clontech, Dean, *Gene Ther.* 10:1465-1470, 2003). The GFP coding region is removed so that a convenient multiple cloning site (MCS) remained for insertion of a selected polynucleotide sequence for expression in osteoblasts. Following transfection using EFFECTENE® transfection reagent, up to 70% transfection efficiency is observed for this plasmid.

Figure 4:
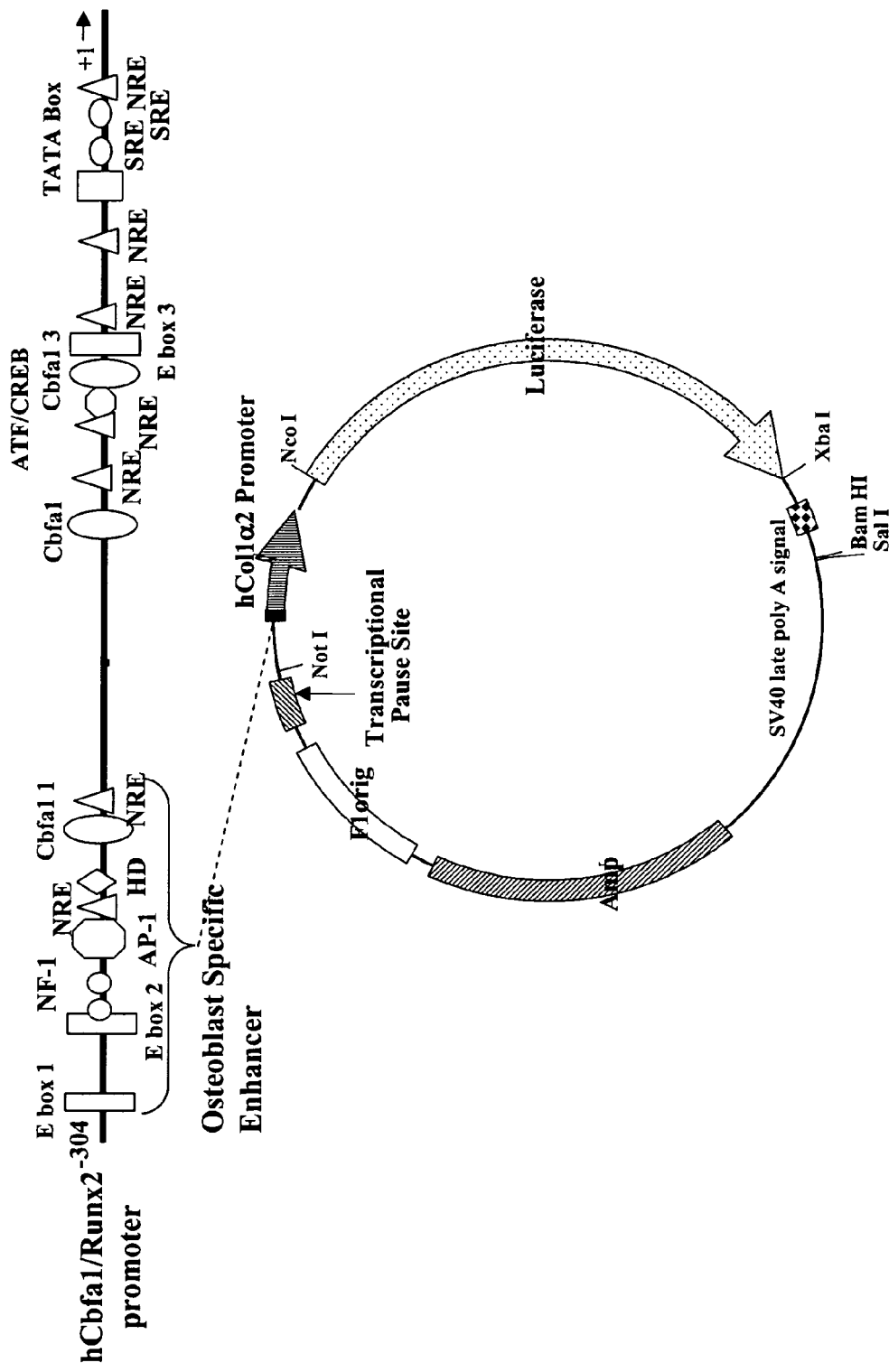
FIG. 4 is a schematic illustration of the structure of a hCbfa1/Runx2-hCol1a2 chimeric promoter construct.

Molecules using an osteoblast-specific nuclear entry sequence, or promoter sequence, such as those derived from the hCol1a2 gene, in combination with the enhancers SEQ ID NOs:2-4 are capable of osteoblast-specific targeting of a DNA molecule to the nucleus with subsequent expression of a transgene. In particular, the osteoblast-specific nuclear entry sequence and promoter sequence SEQ ID NO:1, in combination with one or more of the enhancers SEQ ID NOs:2-4 result in osteoblast-specific targeting of a DNA molecule to the nucleus with subsequent robust expression of a transgene. An exemplary plasmid vector including these sequences is found in FIG. 4. Such a plasmid can be prepared using well known molecular biology procedures, such as those described in Sambrook et al., *Molecular Cloning: A Laboratory Manual*, Cold Spring Harbor Laboratory Press, Cold Spring Harbor, N.Y., 2001; and Ausubel et al. *Short Protocols in Molecular Biology*, 4th ed., John Wiley & Sons, Inc., 1999. For example, a fragment of the human Cbfa1/Runx2 proximal promoter can be prepared by PCR with primer sets as described in reference to FIG. 3.

Numerous nucleotides connecting SEQ ID NO:1 with SEQ ID NOs:2-4 are likely to be filler or spacer nucleotides which are not critical to function. An A or G which is such a filler or spacer nucleotide can readily be interchanged with a C or T, for example, without affecting the function of the molecule. Such nucleotides can also readily be deleted. Additional nucleotides 5' or 3' to the SEQ ID NO:1 in the hCol1α2 promoter as exemplified by SEQ ID NO:2-4, can be added without detracting from the molecule's cell-specific nuclear targeting function.

As used herein, a nucleic acid sequence which has a sequence substantially as shown in a particular SEQ ID NO refers to a nucleotide sequence which is substantially the same, or has substantial sequence identity to, e.g., is homologous to, the designated nucleotide sequence. In some embodiments, particularly where SEQ ID NO:1 is used for its osteoblast nuclear entry properties, substantially the same nucleotide sequence means a nucleotide identity of at least about 95%, or at least about 96%, often at least about 98%, or even about 99%, or greater. In some embodiments, particularly where SEQ ID NO:1 is used as a promoter to drive transgene expression, substantially the same nucleotide sequence means a nucleotide identity of about 80%, or 85%, or 90% or 95% or greater (as indicated above). In general, as used herein, a substantially similar polynucleotide sequence, e.g., a homologous sequence, is one which has the described percentage nucleotide identity, or one which is functionally substantially the same as the given sequence.

Methods of determining sequence identity are well known in the art. Various programs and alignment algorithms are described in: Smith and Waterman, *Adv. Appl. Math.* 2:482, 1981; Needleman and Wunsch, *J. Mol. Biol.* 48:443, 1970; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Another indicia of sequence similarity between two nucleic acids is the ability to hybridize. The more similar are the sequences of the two nucleic acids, the more stringent the conditions at which they will hybridize. The stringency of hybridization conditions are sequence-dependent and are different under different environmental parameters. Thus, hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found, for example, in Sambrook et al., *Molecular Cloning: A Laboratory Manual*, Cold Spring Harbor Laboratory Press, Cold Spring Harbor, N.Y., 2001; Tijssen, *Hybridization With Nucleic Acid Probes, Part I: Theory and Nucleic Acid Preparation*, Laboratory Techniques in Biochemistry and Molecular Biology, Elsevier Science Ltd., NY, N.Y., 1993. and Ausubel et al. *Short Protocols in Molecular Biology*, 4th ed., John Wiley & Sons, Inc., 1999.

For purposes of the present disclosure, "stringent conditions" encompass conditions under which hybridization will only occur if there is less than 25% mismatch between the hybridization molecule and the target sequence. "Stringent conditions" can be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize. In contrast nucleic acids that hybridize under "low stringency conditions include those with much less sequence identity, or with sequence identity over only short subsequences of the nucleic acid.

Additions, deletions, and substitutions can be made by methods known in the art, including PCR and site-directed mutagenesis.

Expressing Transgenes in Osteoblast Lineage Cells

The nuclear targeting or entry molecule is readily used by providing a nucleic acid, such as a plasmid or a viral vector, including the osteoblast-specific nuclear targeting sequence for targeting a polynucleotide sequence into the nucleus of an osteoblast lineage cell. A linear DNA molecule, e.g., derived from a plasmid or created by Polymerase Chain Reaction (PCR), can also be readily used for targeting the nucleic acid into osteoblast nuclei. The nucleic acid, e.g., plasmid vector, viral vector or linear DNA, in their most basic forms, include a cell-specific nuclear targeting molecule having a nucleic acid sequence which includes binding sites for DNA binding proteins with NLSs that are expressed only in osteoblasts. Typically, the nucleic acid also includes a polynucleotide sequence that can be expressed (e.g., as a polypeptide or RNAi, siRNA or antisense RNA). For convenience, such a polynucleotide sequence is referred to herein as a transgene. Generally, the transgene is operably linked to the polynucleotide sequence with the osteblast-specific nuclear targeting sequence. One embodiment uses the hColl$\alpha$2 nuclear entry/promoter (e.g., SEQ ID NO:1) upstream of the transgene. An osteoblast specific enhancer sequence can be upstream or downstream of the hColl$\alpha$2 nuclear entry/promoter and transgene. In the case of a circular DNA molecule, upstream and downstream are given meaning in relation to a specified polynucleotide sequence (or gene). In another embodiment, the hColl$\alpha$2 nuclear entry/promoter sequence can be used alone for osteoblast specific nuclear entry. Optionally, in this embodiment, after nuclear entry, transgene expression is directed by constitutively expressed promoters (CMV, RSV) or from inducible promoters (stimulated by tetracycline, ecdysone, RU486 or rapamycin) as is well known in the art (Clackson, *Gene Ther.* 7:120-125, 2000).

The transgene to be targeted to the nucleus can encodes one or more polypeptides to be expressed in an osteoblast. In general, any nucleic acid that directly or indirectly results in a beneficial effect is considered to be within the scope of the present disclosure. Numerous examples of transgenes suitable for expression in osteoblast lineage cells are known to those of ordinary skill in the art, and include, for example growth factors, hormones, cytokines, transcription factors, enzymes, metal (e.g., calcium, magnesium) binding proteins, and structural proteins, e.g., FGFs, IGFs, TGF$\beta$, VEGFs, BMPs, cyclooxygenase-2, LMPs, IGFBPs, TWIST, Cbfa1/Runx2, osterix, IL-17B, type I alpha (1 or 2) procollagen, calcitonin, osteopontin, osteonectin, RANK ligand, osteoprotegerin etc. Likewise, polypeptides that interact with or bind to such cellular polypeptides can be encoded by the heterologous polynucleotide sequence. These molecules include those that encode therapeutic proteins, as well as proteins that can serve as reporters, markers (e.g., diagnostic markers) and proteins that can be used for selection of cells (e.g., antibiotic resistance genes).

In certain embodiments, the transgene is a polynucleotide sequence that encodes a reporter. Reporters include a variety of molecules that can easily be detected by optical or other means. For example, common reporters include the green-fluorescent protein (GFP) of *Aequoria victoria*, *Renilla reniformis*, and *Renilla mullerei* and numerous variants thereof with enhanced or altered excitation and/or emission characteristics. Exemplary GFPs suitable as reporters in the context of this disclosure include without limitation GFPs and variants described by Chalfie et al. *Science* 263: 802-805, 1994; Heim et al. *Proc Natl Acad Sci USA* 91:12501-4, 1994; Heim et al. *Nature* 373:663-4, 1995; Peelle et al., *J. Protein Chem* 20:507-19, 2001; Labas et al. *Proc Natl Acad Sci USA* 99:42564261, 2002, and in U.S. Pat. Nos. 6,818,443; 6,800,733; 6,780,975; 6,780,974; 6,723,537; 6,265,548; 6,232,107; 5,976,796; and 5,804,387. Red fluorescent proteins are described in, e.g., U.S. Pat. No. 6,723,537. Such fluorescent proteins can be optically detected using, for example, flow cytometry. Flow cytometry for GFP is described in, e.g., Ropp et al. *Cytometry* 21:309-317, 1995, and in U.S. Pat. No. 5,938,738. Other suitable detection methods include a variety of multiwell plate fluorescence detection devices, e.g., the CYTOFLUOR 4000® multiwell plate reader from Applied Biosciences. Other reporters include proteins with enzymatic activities that convert a fluorogenic or chromogenic substrate into a fluorescent or visible product. Examples of such enzymatic reporters include various naturally occurring and modified luciferases. Exemplary luciferases are described in the following U.S. Pat. Nos. 6,552,179; 6,436,682; 6,132,983; 6,451,549; 5,843,746 (biotinylated); U.S. Pat. No. 5,229,285 (thermostable) and U.S. Pat. No. 4,968,613. U.S. Pat. No. 5,976,796 describes a luciferase-GFP reporter. Additional examples of reporters with enzymatic activity include, e.g., chloramphenicol acetyltransferase (CAT), $\beta$-glucuronidase, $\beta$-galactosidase and alkaline phosphatase.

The DNA molecule to be targeted can also express an RNA that does not code for a protein. Examples of such functional RNA molecules include "antisense oligonucleotide", SiRNA and mRNA that can inhibit the translation or stability of a cellular mRNA, or a stable RNA such as a tRNA, a rRNA, a UsnRNA (involved in mRNA splicing), or 7SL RNA which is part of the signal recognition particle (SRP) for protein translocation into the endoplasmic reticulum. Antisense RNAs, siRNAs and mRNAs are very popular for their potential to alter cellular mRNA levels for desired genes. Another example is "ribozymes," catalytic RNAs that repair mutant mRNAs or cleave mRNAs (Sullenger & Gilboa, *Nature* 418: 252, 2002; Suzuki, *Gene Ther* 7:241, 2000; Scanlon, *J Nat Cancer Inst* 90:558, 1998.

A wide variety of genetic material can be transferred by the compositions and methods of the present disclosure. For example, the nucleic acid segment can be DNA (double or single-stranded); or any type of RNA. Functionally, the nucleic acid can by a coding segment which encodes for a protein, peptide, enzyme etc of interest, or it can be an antisense, or interfering RNA, to mitigate, prevent or disrupt particular gene expression.

The nucleic acid, e.g., plasmid vector, viral vector or linear DNA molecule, of the present disclosure can contain other elements, in addition to the osteoblast-specific nuclear entry polynucleotide sequence and promoter polynucleotide sequence, to direct expression and the gene (nucleic acid) of interest or RNA molecule to be delivered. For example, it can be desirable to include a bacterial origin of replication (such as oriC) for replication of the plasmid in *Escherichia coli*, or the origin of replication of *Bacillus subtilis* for replication therein, or the origin of replication of *Pseudomonas aeruginosa* for replication therein, etc.) so that the plasmid can be maintained and replicated in a bacterial host. Such an embodiment of the plasmid of the present disclosure can also include a selection marker for selecting bacterial colonies which contain the subject plasmid. Such selection or biological markers are well known in the art. In bacteria, these are commonly drug-resistance genes. Drug or antibiotic resistance is used to select bacteria that have taken up cloned DNA from the much larger population of bacteria that have not.

A selection marker can also be included in the plasmid to identify mammalian cells which have taken up the plasmid DNA or to enrich for these cells. For example, the herpes simplex virus thymidine kinase (HSV tk) gene can be used as a selectable genetic marker in mammalian cells in much the same way that drug-resistance genes work in bacteria, to allow rare transfected cells to grow up out of a much larger population that did not take up any DNA. The cells are transferred to selective growth medium, which permits growth only of cells that took up a functional tk gene (and the transferred DNA of interest). Various dominant selectable markers are now known in the art, including: zeocin, an antibiotic of the bleomycin family causing cell death by intercalating into DNA and cleaving it, the Sh Ble gene confers resistance by binding to the antibiotic and preventing its binding to DNA, and blasticidin, a potent translational inhibitor or prokaryotic and eukaryotic cells, resistance is conferred by two Blasticidin S deaminase genes: BSD or bsr which convert Blasticidin S to a non-toxic deaminohydroxy derivative. Numerous other non-limiting examples are disclosed in Dean et al, U.S. Pat. No. 6,130,207, incorporated herein by reference.

Various methods can be employed to increase levels of the transfected genes having the cell specific nuclear-entry capacity. For example, gene amplification can also be used to obtain very high levels of expression of transfected genes. When cell cultures are treated with methotrexate (MTX), an inhibitor of a critical metabolic enzyme, DHFR, most cells die, but eventually some MTX-resistant cells grow up. A gene to be expressed in cells is cotransfected with a cloned dhfr gene, and the transfected cells are subjected to selection with a low concentration of MTX. Resistant cells that have taken up the dhfr gene (and, in most cases, the cotransfected gene) multiply. Increasing the concentration of MTX in the growth medium in small steps generates populations of cells that have progressively amplified the dhfr gene, together with linked DNA. Although this process takes several months, the resulting cell cultures capable of growing in the highest MTX concentrations will have stably amplified the DNA encompassing the dhfr gene a hundredfold or more, leading to significant elevation of the expression of the cotransfected gene.

Cell selection can also be achieved with expression of fluorescent protein products coexpressed with the transgene or as a fusion with the transgene. Cells expressing the fluorescent protein products are selected by FACS (fluorescence activated cell sorting).

Specific initiation signals are also important for efficient gene transcription and translation in procaryotic cells. These transcription and translation initiation signals can vary in "strength" as measured by the quantity of gene specific messenger RNA and protein synthesized, respectively. The DNA expression vector, which contains a promoter, can also contain any combination of various "strong" transcription and/or translation initiation signals. For instance, efficient translation in *E. coli* requires a Shine-Dalgarno (SD) sequence about 7-9 bases 5' to the initiation codon (ATG) to provide a ribosomal binding site. Thus, any SD-ATG combination that can be utilized by host cell ribosomes can be employed. Such combinations include but are not limited to the SD-ATG combination from the CRO gene or the N gene of coliphage lambda, or from the *E. coli* tryptophan E, D, C, B or A genes. Additionally, any SD-ATG combination produced by recombinant DNA or other techniques involving incorporation of synthetic nucleotides can be used.

One embodiment of the present disclosure includes a specific eukaryotic Kozak sequence that stimulates translation effectively in osteoblasts. This sequence can be used in combination with the osteoblast-specific nuclear entry/promoter and/or promoter-enhancer sequences described herein (e.g., with the hCol1α2 nuclear entry/promoter sequence, SEQ ID NO:1, and/or the hCol1α2-hCbfa1/Runx2 chimeric promoters) to enhance translation of the transgene in osteoblasts. An exemplary Kozak sequence is GCCGCCATG(A/G) (SEQ ID NO:5).

In accordance with the present disclosure, the DNA of the plasmid vector, viral vector or the linear DNA molecule as described herein is targeted into the nuclei of osteoblasts, where the transgene or transgenes of the vector are expressed. Since the nuclear-localized DNA will eventually be degraded or diluted by continued cell proliferation, it can be desirable for long-term expression of the DNA molecule in the nuclei of the specific cell type to integrate the DNA into the genome of the specific cell type. In such an embodiment, the DNA of the present disclosure further includes a molecule to direct integration of the DNA molecule into the osteoblast genome. Such integration sequences are known in the art, and include, for example, the inverted terminal repeats of adeno-associated virus (ITRs), retroviral long terminal repeats (LTRs), other viral sequences shown to cause incorporation or integration of the viral genome into the specific cell type genome and the Tcl-like transposon *Sleeping Beauty* (Harris J W, Strong D D, Amoui M, Baylink D J, Lau K H, 2002. *Anal Biochem* 310(1):15-26. As should be readily apparent, various additional elements can be included in the DNA molecules or plasmid vectors of the present disclosure depending upon the desired goal. For ease in constructing various embodiments of the plasmid vector or linear DNA molecule, (comprising the cell-specific nuclear targeting molecule and the DNA molecules to be targeted and expressed) can also contain a number of unique restriction enzyme sites for insertion of the additional molecules or elements. As used herein, a "unique" restriction enzyme site refers to the presence of only one cleavage site for a particular restriction endonuclease within the plasmid or linear DNA. That particular restriction endonuclease (or restriction enzyme) will, therefore, only cleave the DNA of the plasmid at that one location or "unique" site. These unique restriction sites can be provided in the plasmid or linear DNA of the present disclosure by including a polylinker as an element of the DNA molecule. As used herein, a "polylinker" refers to a sequence which contains many restriction enzyme recognition sequences ("restriction sites"). Typically the restriction enzyme recognition sequences present in a polylinker are present only once in the plasmid vector or linear DNA molecule, that is, they are unique restriction sites. The DNA molecule of the present disclosure can also contain restriction sites (for the same enzyme) that occur twice in close proximity (e.g., the flanking sites of the polylinker) and these can also be used to insert (or remove) sequences between the sites.

Having constructed the vector or linear DNA molecule according to the present disclosure, a host cell comprising the vector or linear DNA is also provided by the present disclosure. As indicated above, for maintenance and propagation of the vector, a bacterial host cell (such as *Escherichia coli*) can be used. Bacterial host cells for maintenance and propagation offer the advantages of being easy to work with and capable of rapid reproduction and therefore propagation of the plasmid.

In use however, the DNA molecule to be targeted to the nucleus of an osteoblast is most likely to express a product useful in animals, such as companion pets (including, mammals, birds, amphibians, and reptiles) or host cells. Suitable host cells are any osteoblast lineage cells into which it is desirable to introduce a transgene. For example, the host cell can be an osteoblast or osteoblast lineage cell in vitro or in vivo, e.g., at the site to be treated or prevented by gene therapy for accelerated fracture repair, for osteoporosis or other bone diseases. Osteoblast lineage cells can be a suitable host cell for expression of growth factors, structural proteins, matrix proteins or enzymes that exert a favorable effect on bone growth, maintenance and/or repair, e.g., that stimulate bone formation. The importation of a nucleic acid into the nucleus of an osteoblast can also be desirable in vitro, using primary osteoblast lineage cells (such as cells isolated from the bone marrow of a subject, and optionally enriched or purified for the presence of osteoblast lineage cells) or various cells lines known in the art, such as, for example, the mammalian cells identified as hFOB, C2C12, 7F2, ROS 17/2.8, SaOS-2, TE-85, MG-63, U-2 OS and MC3T3-E1 cells.

A viral vector can provide the means for introducing the DNA/RNA with the transgene to be expressed into the osteoblast. For example, linear DNA molecules containing SEQ ID NO:1 with or without SEQ ID NOs:2-4, can be introduced into viral vectors that do not efficiently transduce nondividing cells because they do not have intrinsic nuclear entry sequences. These include but are not limited to an adenovirus, retrovirus, adeno-associated virus, vaccinia virus, papovavirus, or herpes simplex virus vector. Inclusion of the hCol1α2-derived nuclear entry/promoter and/or the hCol1α2-derived nuclear entry/promoter with a hCbfa1/Runx2-derived enhancer, or SEQ ID NO:1 with any or all of SEQ ID NOs:2-4, into these viral vectors will stimulate viral DNA movement into nucleus of an osteoblast and facilitate transgene expression.

The nuclear targeting molecule of the present disclosure also offers the advantage of being able to target a DNA molecule to the nucleus of nondividing osteoblasts. Nondividing cells include two classes of cells: those that are not dividing (quiescent) and those that cannot divide. When cells leave mitosis and are finished dividing, they enter the G1 phase of the cell cycle and then come to a halt at G0 (G zero). At this point they are "growth-arrested;" transcription and protein synthesis are decreased. Upon stimulation, most cells will exit G0 and continue on with the cell cycle, leading to division. However, many cells will remain in this G0 state for a long time. Human osteocytes do not divide, and osteoblasts divide every one to six days or longer. The period of quiescence for each type of cell is different and depends on its location within the tissue. For cells that do not divide daily or weekly, the molecules, constructs and methods of the present disclosure are especially favorable because plasmid (nonviral) gene deliver in vivo is not very efficient or effective in vivo. The hCol1a2 nuclear entry/promoter sequence increases efficiency of plasmid delivery in vivo and restricts nuclear uptake to the desired cell types within the organism.

Various methods are known in the art for introducing nucleic acid molecules into host cells (including osteoblast lineage host cells). These methods can be used to introduce nucleic acids containing osteoblast-specific nuclear targeting sequences into osteoblast lineage cells (e.g., into the cytoplasm of an osteoblast lineage cell).

For example, lipid mediated transformation can be utilized to obtain efficient introduction of nucleic acids including a osteoblast-specific nuclear targeting sequence. Liposomal or non-liposomal lipid formulations can be combined with purified nucleic acids to form complexes which are then added to osteoblast lineage cells, where the lipid-DNA complexes fuse with the cell membrane, mediating cellular uptake of the nucleic acid. For example, one lipid reagent that has proven particularly effective for transforming osteoblast lineage cells is the non-liposomal EFFECTENE® Reagent (Qiagen, Valencia, Calif.). Using EFFECTENE® according to manufacturer's directions, nucleic acids including an osteoblast-specific nuclear targeting can be targeted to the nucleus of non-dividing osteoblast lineage cells with an efficiency of approximately 70%.

Electroporation is a commonly used transformation method that can be utilized conveniently to introduce nucleic acids with osteoblast-specific nuclear targeting sequences into osteoblast lineage cells. Electroporation is well known by those of ordinary skill in the art (see, for example: Lohr et al. *Cancer Res.* 61:3281-3284, 2001; Nakano et al. *Hum Gene Ther.* 12:1289-1297, 2001; Kim et al. *Gene Ther.* 10:1216-1224, 2003; Dean et al. *Gene Ther.* 10:1608-1615, 2003; and Young et al. *Gene Ther* 10:1465-1470, 2003). Generally, in electroporation, a high concentration of vector DNA is added to a suspension of host cell and the mixture shocked with an electrical field. Transcutaneous electroporation can be utilized in animals and humans to introduce heterologous nucleic acids into osteoblast lineage cells in vivo. Typically, between 10 and 500 µg of DNA (e.g., including an osteoblast-specific nuclear targeting sequence) is introduced into osteoblast lineage cells of skeletal tissue by introducing a solution containing the DNA into the skeletal tissue, e.g., using a needle or trochar in conjunction with electrodes for delivering one or more electrical pulses. For example, a series of electrical pulses can be utilized to optimize transfection, e.g., between 3 and ten pulses of 100V and 50 msec. In some cases, multiple sessions or administrations are performed.

Another well known method that can be used to introduce nucleic acids containing osteoblast-specific nuclear targeting sequences into host cells is particle bombardment (also know as biolistic transformation). Biolistic transformation is commonly accomplished in one of several ways. Once common method involves propelling inert or biologically active particles at cells. This technique is disclosed in, e.g., U.S. Pat. Nos. 4,945,050, 5,036,006, and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the plasmid can be introduced into the cell by coating the particles with the plasmid containing the exogenous DNA. Alternatively, the target cell can be surrounded by the plasmid so that the plasmid is carried into the cell by the wake of the particle.

Another method of introducing nucleic acids with osteoblast-specific nuclear targeting sequences into cells is microinjection, in which DNA is injected directly into the cytoplasm of cells, typically using fine glass needles. Alternatively, DNA can be incubated with an inert carbohydrate polymer (dextran) to which a positively charged chemical group (e.g., diethylaminoethyl, "DEAE") has been coupled. The DNA sticks to the DEAE-dextran via its negatively charged phosphate groups. These large DNA-containing particles stick in turn to the surfaces of cells, which are thought to take them in by a process known as endocytosis. In another method, cells efficiently take in DNA in the form of a precipitate with calcium phosphate.

As previously indicated, the nucleic acids used in the methods described herein can be plasmids. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation (according to any of the methods mentioned above) and replicated in procaryotic and/or eucaryotic cells. The DNA sequences are cloned into the plasmid vector suing standard cloning procedures known in the art, as described by Sambrook et al. (1989).

Linear nucleic acid (e.g., DNA) molecules are also suitable in the context of the methods described herein for introducing nucleic acids into the nuclei of osteoblast lineage cells. Published U.S. Patent Application No. 20030157717 describes the use of expression systems in the form of double-stranded linear DNA fragments with a tissue specific promoter, a transgene, a promoter, a transgene of interest and a 3' untranslated region. The double stranded DNA including the transgene is delivered to tissue of an animal by direct injection accompanied by electroporation. The linear DNA can be obtained from plasmid vectors using restriction enzyme cleavage or by using PCR from the plasmid template using standard procedures known in the art.

Without being limited by theory, a model for the tissue specific import reaction (FIG. 1) has been proposed. The proposed model is based on the DNA sequences involved in the nuclear import of vector DNA. Since transcription factors, like all proteins, are translated in the cytoplasm, they must target to the nucleus either after synthesis or upon proper stimulation. To enter the nucleus they must either contain nuclear localization signals (NLSs) or complex with other proteins that contain an NLS. Since transcription factors bind to specific DNA sequences, if DNA containing the appropriate binding sequences is present in the cytoplasm, it can be complexed by these proteins, thus coating the DNA with protein NLSs. The NLSs present in this nucleoprotein complex can then interact with the normal importin/karyopherin receptor and enter the nucleus by the normal nuclear protein import machinery (Dean, *Exp Cell Res* 253:713, 1999).

Therapeutic Methods

The compositions and methods described herein are favorably utilized to deliver nucleic acids into the nuclei of osteoblast lineage cells for therapeutic or prophylactic treatment of a condition or disease affecting bone metabolism, for example bone growth, bone maintenance and/or bone repair. Thus, the described compositions and methods can be used for skeletal gene therapy. For example, vectors for administering expressible nucleic acids with a beneficial (for example, therapeutic) effect on bone tissue can be generated by incorporating a polynucleotide sequence that encodes a desired product (such as a therapeutic polypeptide or RNA) operably linked to an osteoblast-specific nuclear localization sequence, and optionally, enhancer sequences that confer robust expression in osteoblast lineage cells. Such vectors increase specificity of administration to skeletal tissue, reducing safety concerns and increasing efficacy of gene therapy. In some embodiments, gene therapy is used to increase expression of a target gene. In other embodiments, gene therapy is used to replace a defective copy of a gene of interest. In still further embodiments, gene therapy is used to down-regulate (e.g., inhibit) the expression of a gene that is detrimentally expressed or overexpressed (e.g., through the use of antisense or siRNA technologies). Such applications find use in the treatment of disease (e.g., bone disease) characterized by the aberrant expression of a gene or the presence of a defective copy of a gene.

The nuclear entry sequence can be incorporated into any gene-expression vector to restrict gene targeting and expression to osteoblast lineage cells. Such compositions and methods find use in a variety of applications including but not limited to, gene therapy for the treatment of bone diseases and disorders including fracture repair, osteoporosis, and Osteogenesis imperfecta. Exemplary therapeutic nucleic acids include polynucleotide sequences that encodes ostogenic factors, such as a fibroblast growth factor (e.g., FGF-1-23), insulin-like growth factor 1 or 2 (IGF), Insulin-like Growth Factor binding Protein (IGFBP) 1-7, a transforming growth factor beta (TGFβ), LIM Mineralization Proteins 14 (LMPs), cyclooxygenase-2 (COX-2), a prostaglandin producing enzyme, a vascular endothelial growth factor (VEGF), any one of a number of bone morphogenic proteins (BMPs), TWIST helix-loop-helix proteins, a Runt-related transcription factor 2 (Runx2) or an osterix transcription factor, operably linked to a polynucleotide sequence including an osteoblast-specific nuclear targeting sequence. Similarly, polynucleotide sequences that encode cytokines, such as IL-18 (that inhibits osteoclast proliferation) can be expressed (or overexpressed) in osteoblasts to reduce bone degradation. Nucleic acids including such osteogenic polypeptides operably linked to a polynucleotide sequence with an osteoblast-specific nuclear targeting sequence can be introduced and expressed specifically in osteoblast lineage cells using the methods described herein. In an embodiment, the nucleic acid includes a polynucleotide encoding a type I alpha (1 or 2) procollagen polypeptide. Such a nucleic acid can be introduced into a subject using the methods described herein, for example, to treat osteogenesis imperfecta. In another embodiment, the nucleic acid includes a polynucleotide sequence encoding a LMP polypeptide or a IGFBP-6 SiRNA. Such a nucleic acid can be introduced, e.g., to treat or prevent osteoporosis. In some embodiments, an IGFBP-6 polynucleotide sequence encoding an IGFBP-6 polypeptide can be introduced to treat bone cancer (osteosarcoma, prostate cancer, breast cancer, multiple myeloma and other cancers with high affinity for skeletal tissues). In some embodiments, the polypeptide is a polypeptide that inhibits or interferes with a protein expressed in osteoblast lineage cells. Such polypeptides include dominant negative forms of proteins, binding proteins (such as antibodies and antibody fragments, and soluble receptor molecules), fusion proteins, etc., that interfere with expression or inhibit the activity of proteins, such as IGFBP-6 or IL-17B receptor that increase bone loss. For example, the therapeutic nucleic acids can encode a soluble form of IGFBP-6 or the IL-17B receptor capable of binding IL-17B and preventing bone degradation mediated by this cytokine. In another example, the therapeutic nucleic acids can encode the soluble RANK ligand binding protein osteoprotegerin, preventing bone degradation mediated by RANK ligand.

In other embodiments, the nucleic acid includes a polynucleotide sequence that encodes a functional RNA molecule, such as an antisense RNA, an siRNA, or a ribozyme that diminishes, interferes with or modifies expression of an RNA or protein expressed in osteoblast lineage cells. For example, the nucleic acid can include an siRNA (or other inhibitory RNA molecule) that interferes with, and decreases expression of, a factor that increases bone loss (such as, IGFBP-6, TWIST, IL-17B receptor). Similarly, inhibitory RNAs specific for the interleukin-1 receptor (IL-1R) and/or for RANK ligand can be introduced and expressed in osteoblast lineage cells using the methods described herein to treat osteoporosis. Nucleic acids including a polynucleotide sequence that encodes an inhibitory RNA molecule operably linked to a polynucleotide sequence with an osteoblast-specific nuclear targeting sequence can also be used to treat conditions that result in abnormal overgrowth of bone, such as post-amputation hyperplasia and hereditary hyperostosis syndromes. Favorable targets for interference by siRNA include, for example, osteocalcin, osteonectin, vone sialo protein, LMP, osterix, BMP, FGF, IGF, VEGF and procollagen genes Viral vectors commonly used for in vivo or ex vivo targeting and therapy procedures are retroviral and DNA-based vectors. Methods for constructing and using viral vectors are known in the art (See e.g., Miller and Rosman, *BioTech.*, 7:980-990, 1992). Preferably, the viral vectors are replication defective, that is, they are unable to replicate autonomously in the target cell. In general, the genome of the replication defective viral vectors that are used within the scope of the present disclosure lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques can be performed in vitro (i.e, on the isolated DNA).

In some cases, the replication defective virus retains the sequences of its genome that are necessary for encapsidating the viral particles. DNA viral vectors commonly include an attenuated or defective DNA viruses, including, but not limited to, herpes simplex virus (HSV), papillomavirus, Epstein Barr virus (EBV), adenovirus, adeno-associated virus (AAV), Moloney leukemia virus (MLV) and human immunodeficiency virus (HIV) and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al. *Mol. Cell. Neurosci.*, 2:320-330, 1991), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. (*J. Clin. Invest.*, 90:626-630 1992; La Salle et al., *Science* 259:988-990, 1993); and a defective adeno-associated virus vector (Samulski et al., *J. Virol.*, 61:3096-3101, 1987; Samulski et al., *J. Virol.*, 63:3822-3828, 1989; and Lebkowski et al., *Mol. Cell. Biol.*, 8:3988-3996, 1988).

For example, the gene can be introduced in a retroviral vector (e.g., as described in U.S. Pat. Nos. 5,399,346, 4,650, 764, 4,980,289 and 5,124,263; all of which are herein incorporated by reference; Mann et al., *Cell* 33:153, 1983; Markowitz et al., *J. Virol.*, 62:1120, 1988; PCT/US95/14575; EP 453242; EP178220; Bernstein et al. *Genet. Eng.*, 7:235, 1985; McCormick, *Bio Technol.*, 3:689, 1985; WO 95/07358; and Kuo et al. *Blood* 82:845, 1993). Most retroviruses are integrating viruses that infect dividing cells. The Lentiviruses are integrating viruses that infect nondividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. The gag, pol and env genes are coexpressed in the packaging cell line. These vectors can be constructed from different types of retrovirus, such as, HIV, MoMuLV ("murine Moloney leukemia virus" MSV ("murine Moloney sarcoma virus"); RSV ("Rous sarcoma virus"). In general, in order to construct recombinant retroviruses containing a nucleic acid sequence, a plasmid is constructed that contains the LTRs, the encapsidation sequence and the construct of the present disclosure comprising a nuclear targeting signal and a coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and the GP+envAm-12 cell line (See, WO89/ 07150). In addition, the recombinant retroviral vectors can contain modifications within the LTRs for suppressing transcriptional activity as well as extensive encapsidation sequences that can include a part of the gag gene (Bender et al., *J. Virol.*, 61:1639, 1987). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et al., *Proc. Natl. Acad. Sci. USA* 84:7413-7417, 1987; Mackey et al., *Proc. Natl. Acad. Sci. USA* 85:8027-8031, 1988; Ulmer et al., *Science* 259:1745-1748, 1993). The use of cationic lipids can promote encapsulation of negatively charged nucleic acids, and also promote fusion with negatively charged cell membranes (Felgner and Ringold *Science* 337:387-388, 1989). Particularly useful lipid compounds and compositions for transfer of nucleic acids are described in WO95/18863 and WO96/17823, and in U.S. Pat. No. 5,459,127, herein incorporated by reference.

In one embodiment, the vector is an adenovirus vector. Adenoviruses are eukaryotic DNA viruses that can be modified to efficiently deliver a nucleic acid of the disclosure to a variety of cell types. Various serotypes of adenovirus exist. Of these serotypes, preference is given, within the scope of the present disclosure, to type 2 or type 5 human adenoviruses (Ad 2 or Ad 5), or adenoviruses of animal origin (See e.g., WO94/26914). Those adenoviruses of animal origin that can be used within the scope of the present disclosure include adenoviruses of canine, bovine, murine (e.g., Mav1, Beard et al. *Virol.*, 75-81, 1990), ovine, porcine, avian, and simian (e.g., SAV) origin. In some embodiments, the adenovirus of animal origin is a canine adenovirus, such as a CAV2 adenovirus (e.g., Manhattan or A26/61 strain (ATCC VR-800)).

The replication defective adenoviral vectors described herein include the ITRs, an encapsidation sequence and the nucleic acid of interest. In some embodiments, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions can also be modified, in particular the E3 region (e.g., WO95/02697), the E2 region (e.g., WO94/28938), the E4 region (e.g., WO94/28152, WO94/12649 and WO95/02697), or in any of the late genes L1-L5.

In other embodiments, the adenoviral vector has a deletion in the E1 region (Ad 1.0). Examples of E1-deleted adenoviruses are disclosed in EP 185,573, the contents of which are incorporated herein by reference. In another embodiment, the adenoviral vector has a deletion in the E1 and E4 regions (Ad 3.0). Examples of E1/E4-deleted adenoviruses are disclosed in WO95/02697 and WO96/22378. In still another embodiment, the adenoviral vector has a deletion in the E1 region into which the E4 region and the nucleic acid sequence are inserted.

The replication defective recombinant adenoviruses according to this disclosure can be prepared by any technique known to the person skilled in the art (See e.g., Levrero et al. *Gene* 101:195, 1991; EP 185 573; and Graham *EMBO J.*, 3:2917, 1984). In particular, they can be prepared by homologous recombination between an adenovirus and a plasmid, which includes, inter alia, the DNA sequence of interest. The homologous recombination is accomplished following cotransfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that can be used are the human embryonic kidney cell line 293 (Graham et al., *J. Gen. Virol.* 36:59, 1977), which contains the left-hand portion of the genome of an Ad5 adenovirus (12%) integrated into its genome, and cell lines that are able to complement the E1 and E4 functions, as described in applications WO94/26914 and WO95/02697. Recombinant adenoviruses are recovered and purified using standard molecular biological techniques that are well known to one of ordinary skill in the art.

For in vivo administration, an appropriate immunosuppressive treatment can be employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. No. 4,797,368; U.S. Pat. No. 5,139,941; and EP 488 528, all of which are herein incorporated by reference). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation (e.g., transcutaneous electroporation), microinjection, transduction, cell fusion, DEAE dextran, calcium phosphate precipitation, use of a gene gun, or use of a DNA vector transporter (See e.g., Wu et al., *J. Biol. Chem.*, 267:963-967, 1992; Wu and Wu, *J. Biol. Chem.*, 263:14621-14624, 1988; and Williams et al., *Proc. Natl. Acad. Sci. USA* 88:2726-2730, 1991). Receptor-mediated DNA delivery approaches can also be used (Curiel et al., *Hum. Gene Ther.*, 3:147-154, 1992; and Wu and Wu, *J. Biol. Chem.*, 262:4429-4432, 1987).

Defects in the process of bone repair and regeneration are linked to the development of several human diseases and disorders, e.g., osteoporosis and osteogenesis imperfecta. The process of bone repair/regeneration includes hemorrhage; clot formation; dissolution of the clot; ingrowth of the granulation tissue; formation of cartilage; capillary ingrowth and cartilage turnover; rapid bone formation and remodeling of callus into cortical and trabecular bone. Regulatory factors involved in bone repair include systemic hormones, cytokines, growth factors and others. Many polypeptide osteoinductive agents are known: for example, BMPs.

The methods described herein can be employed to promote expression of a desired gene (one of the classes encompassed by the phrase "nucleic acid of interest") and thus impart a desired phenotype to the cells. The gene can be a structural gene, either endogeneous or exogenous, resulting in a particular gene product. Such gene product can be partly or wholly expressed by the transferred gene, or can supplement a naturally expressed product. The transferred gene can also be used to suppress the expression of a gene (or gene product) that the target cell expresses in its natural, or unmodified state. This can be accomplished, for example, by expressing (or increasing expression of) a protein that down-regulates the gene of interest, or by antisense, ribozyme or RNAi techniques. Non-limiting examples include osteotropic genes such as BMPs, Insulin-like Growth Factors, Insulin-like growth factor binding proteins (IGFBPs), FGFs, TGFβ, PTH, VEGF, BMPs, (these are inhibitors of differentiation) Cbfa1/Runx2, osterix, IL-17B, type I alpha (1 or 2) procollagen, calcitonin, osteopontin, Lim Mineralization Protein (LMP)-1 or -3, Cyclooxygenase-2, etc.

Screening Methods

Osteoblast specific gene transfer and expression is also useful to produce model systems for drug screening (e.g., in cell culture and animal models). For example, in some embodiments, the present disclosure provides methods and compositions utilizing the nuclear entry sequence of the present disclosure to alter expression of a gene of interest to produce a cellular or animal (e.g., mouse) model of a human disorder affecting bone metabolism. The cellular and animal models are useful in methods for identifying agents that ameliorate the condition and/or that exert a favorable effect on bone metabolism, e.g., bone growth, bone maintenance, fracture repair, etc. In addition, such models are useful for evaluating potential gene therapies prior to their evaluation in human subjects.

For example, the methods of the present disclosure can be used to generate cells (e.g., osteoblasts) that express or repress expression of a transgene of interest (e.g., as discussed above). Drug screening is facilitated when the expression of the nucleic acid encoded by the constructs of the present disclosure generates a cell or animal that mimics a disease state. Test compounds are then administered to the cell or animal and the effect of the test compounds on the disease state is monitored. A therapeutic drug need not directly inhibit or stimulate a target's activity, but can also be effective by redistributing or mis-targeting a drug target, e.g., an enzyme, structural protein, transport protein etc.

The test compounds of the present disclosure can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckermann et al., *J. Med. Chem.* 37: 2678-85, 1994); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam, *Anticancer Drug Des.* 12:145, 1997).

Examples of methods for the synthesis of molecular libraries can be found in the art, for example in: DeWitt et al., *Proc. Natl. Acad. Sci. U.S.A.* 90:6909, 1993; Erb et al., *Proc. Nad. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33.2059, 1994; Carell et al., *Angew. Chem. Int. Ed. Engl.* 33:2061, 1994; and Gallop et al., *J. Med. Chem.* 37:1233, 1994.

Libraries of compounds can be presented in solution (e.g., Houghten, *Biotechniques* 13:412-421, 1992), or on beads (Lam, *Nature* 354:82-84, 1991), chips (Fodor, *Nature* 364: 555-556, 1993), bacteria or spores (U.S. Pat. No. 5,223,409), plasmids (Cull et al., *Proc. Nad. Acad. Sci. USA* 89:1865-1869, 1992) or on phage (Scott and Smith, *Science* 249:386-390, 1990; Devlin *Science* 249:404-406, 1990; Cwirla et al., *Proc. Natl. Acad. Sci. USA* 87:6378-6382, 1990; Felici, *J. Mol. Biol.* 222:301, 1991).

The present disclosure is not limited to the drug screening and gene therapy applications described above. As described above, the constructs of the present disclosure can be used to generate cells or animals that mimic a disease state. The methods of the present disclosure can be used in research application to further elucidate disease or metabolic pathways (e.g., through altering expression of a gene of interest and monitoring the resulting phenotype). In some embodiments, disease states are mimicked by increasing expression of a gene of interest (transgene). In some embodiments, disease states are mimicked by reducing expression of a gene of interest (transgene) (e.g., through antisense or siRNA applications). Methods of producing transgenic animals are well-known in the art, and suitable protocols, e.g., for the production of transgenic mice, can be found in, e.g., Hogan et al., *Manipulating the Mouse Embryo*, Cold Spring Harbor Press, 1994. For example, nucleic acids including an osteoblast-specific nuclear targeting sequence can be introduced into fertilized oocytes by microinjection. The oocytes are implanted into pseudopregnant females, and the litters are assayed for insertion of the transgene. In some cases, the polynucleotide sequence to be expressed encodes a polypeptide with a desired enzymatic or structural attribute, expression of which is desired in ostoblast lineage cells. In other cases, the polynucleotide sequence encodes a polypeptide capable of modulating, e.g., reducing activity or expression of an endogenous gene product. Examples of such polypeptides, which can be introduced (and expressed) under the control of an osteoblast-specific nuclear targeting sequence include dominant negative polypeptides, fusion polypeptides, antibodies and other binding proteins. Similarly, the polynucleotide can include a functional RNA, the expression of which in osteoblast lineage cells is desirable. Functional RNAs include, for example, antisense RNAs, siRNAs, smRNAs and ribozymes.

For example, transgenic mice (as well as cultured cells), the P1 bacteriophage enzyme Cre recombinase (Cre) catalyzes the rearrangement of DNA fragments flanked by 34 bp loxP sites ("floxed"), and efficiently excises any DNA sequences between the loxP recognition sites (see, e.g., Lakso et al., *Proc. Natl. Acad. Sci. USA* 89:6232-6236, 1992; Kuhn et al., *Science* 269:1427-1429, 1995). Many important genes have been floxed and transgenic mice containing these genes are readily available. Breeding Cre transgenic mice with loxP transgenic mice produces progeny in which the floxed gene of interest is deleted in all cells expressing Cre. Putting Cre expression under control of an osteoblast-specific promoter makes it possible to obtain tissue specific gene knockouts or tissue specific gene activations in mice. Thus, any of the gene targets described herein can be modulated in a tissue specific manner in transgenic mice by placing the Cre recombinase under the control of the type I procollagen promoter region or this region as a chimera with the hCbfa1/Runx2 enhancer. Such mice can then be interbred with mice having a target gene of interest flanked by loxP sites. Cre activated homologous recombination can then be used to modulate (e.g., inactivate) the target gene in the bone of transgenic mice.

Additionally, the osteoblast-specific nuclear entry sequence, e.g., in the context of a hCol1α2-Cre expression vector, provides the means to increase Cre recombinase expression only in osteoblast lineage cells in transgenic mice having a floxed target gene of interest following localized introduction of the vector in or near skeletal tissue. This approach offers the advantage that laborious breeding of the osteoblast specific Cre transgenic mice to the floxed target gene mice can be eliminated. This vector can be used to increase Cre expression, effecting gene deletion or activation, in individual bones or bone sites (e.g., sites of fracture) by injecting the hCol1α2-Cre vector, e.g., with electroporation (such as transcutaneous electroporation, twizzertrode or needletrode electroporation across or within the skeletal site) or with a lipid-based gene transfer systems. The effect of local gene deletion or activation on skeletal metabolism can then be observed in transfected and non-transfected bone in the same animal. This approach can be utilized both for identifying exogenous agents that impact bone metabolism (e.g., fracture repair, osteoarthritis) and for identifying genes important in normal and disease associated skeletal metabolism and to develop treatment paradigms for bone diseases and fracture repair.

Kits

The present disclosure further contemplates a kit or article of manufacture, for osteoblast-specifically promoting transgene expression of a given product; for osteoblast-specific nuclear entry, or for combinations thereof. The kit can be promoted, distributed, or sold as a unit for performing the methods of the present disclosure. The kit includes: (i) a plasmid containing the osteoblastic-specific nuclear-entry sequence, e.g., derived from the hColIa2 gene as described herein, a multiple cloning site (MCS) and a selectable marker, and optionally a poly A addition site, and/or an enhancer sequence to increase expression in osteoblasts. The kit can also optionally include instructions for use.

EXAMPLES

Example 1

Preparation of the hCol1α2 Promoter

The human type I alpha 2 procollagen (hCol1α2) promoter (−267 to +45) was prepared by PCR from an anonymous human genomic DNA sample and was subcloned into the pGL3$_{Basic}$ vector from Promega (Madison, Wis.). The DNA was purified from a blood sample using the PureGene Kit (Gentra). The human collagen promoter was prepared with Pfu DNA Polymerase (Stratagene, La Jolla, Calif.) and with the oligonucleotides: tcgagacaacgagtcagagt; SEQ ID NO:29 and gccagtacctccaacttagc; SEQ ID NO:30, in an MJ Research thermocycler. The PCR product was cloned into the pCR Blunt Vector (Invitrogen, Carlsbad, Calif.), transformed into Top 10 one shot cells (Invitrogen) and grown on Kanamycin plates. DNA was purified and sequenced. The promoter fragment (−267 to +45) was removed from the pCR Blunt vector with Kpn I and Xho I and was subcloned into the pGL3$_{Basic}$ vector at the Kpn I site and Xho I sites for testing of basal promoter activity and nuclear entry activity.

Example 2

Analysis of Basal Promoter Activity and Osteoblast Expression Specificity

The hCol1α2 promoter was one of several promoters tested and compared for strength of basal activity and specificity of expression in rat and human osteoblasts, rat fibroblasts, rat marrow stromal cells and rat chrondrocytes. Table 1 illustrates the activities of these promoters expressed in osteoblasts. The osteoblast promoters were not expressed in other cell types. The hCol1α1, hCol1α2 and Cbfa1/Runx2 promoters were the most strongly and specifically expressed in osteoblasts.

TABLE 1

Analysis of promoter and nuclear entry activity in ROS 17/2.8 cells.

| Sample | Osteoblast Promoter | Gene Region | Promoter Activity in Osteoblasts (as % of mouse Osteocalcin Promoter) | Nuclear Entry Activity (as % of Cells with fluorescent nucleus) |
|---|---|---|---|---|
| 1 | m osteocalcin | −1393 to +18 | 100 | 0 |
| 2 | h osteocalcin | −345 to +28 | 84 | 0 |
| 3 | hCol1α1 | −290 to +172 | 120 | 0 |
| 4 | hCol1α2 | −267 to +45 | 247 | 30-40 |
| 5 | hCol1α2 | −107 to +45 | 10 | 0-1 |
| 6 | rCol1α1 | −2050 to +119 | 300 | 0 |
| 7 | hBSP | −1917 to +44 | 104 | 0-1 |
| 8 | hCbfa1/Runx2 | −5 to +347 | 16 | 0 |
| 9 | hCbfa1/Runx2 | −2060 to +8 | 240 | 0 |
| 10 | hCbfa1/Runx2 | −345 to +8 | 260 | 0 | m = mouse,
r = rat,
h = human.

Promoter activity of the sample was compared to mouse osteocalcin promoter (sample #1) It can be seen that samples 4, 6, 9 and 10 exhibited much greater activity than the standard, and samples 3 and 7 slightly greater activity. With regard to nuclear entry, only sample 4 (hCol1α2) was significant. Generally osteoblast-specific promoter activity is within the scope of the present disclosure if the activity is greater than 120% or greater than 200%, or greater than 250%, or greater than 300% of the mouse osteocalcin promoter. Nuclear entry of a given sequence is considered within the scope of the present disclosure if it is at least 20% or 30% or 40% efficient. One way in which nuclear entry efficiency, or activity, can be measured is by fluorescence as described herein, and as further known in the art. For all of the promoters except hCol1α2 and BSP there was no nuclear entry in 3-5 independent experiments. The range of 30-40% activity for the hCol1α2 nuclear entry/promoter sequence was determined by five independent experiments. Each osteoblast marker gene promoter was linked to the luciferase reporter in the pGL3$_{Basic}$ vector (Promega). ROS 17/2.8 cells were cotransfected with the pGL3-osteoblast promoter vector and the CMV-β-gal vector (Clontech) to normalize transfection efficiency using EFFECTENE® transfection reagent (Qiagen). The osteoblast promoter activated luciferase activity and was normalized to β-galactosidase activity produced from the cotransfected CMV-β-gal plasmid vector. The CMV promoter that drives β-gal expression does not have nuclear entry activity. Normalized promoter activity from all of the osteoblast promoters was then expressed as a % of the activity of the mouse osteocalcin promoter.

Example 3

Demonstration that the Type I Alpha 2 Procollagen (hCol1α2) Promoter has Intrinsic Nuclear Entry Activity To determine whether any of the osteoblast marker gene promoters can enter the osteoblast nucleus without cell division, protein-free supercoiled plasmid (P) DNA was prepared from the hCol1α1, hCol1α2, hBSP, Cbfa1/Runx2 and human osteocalcin promoters in the pGL3$_{Basic}$ vector. pGL3$_{Basic}$ plasmid vector or vector with the pGL3$_{Basic}$ vector containing the hCol1α2 promoter was injected into the cytoplasm of ROS 17/2.8 osteoblast-like osteosarcoma cells (approximately 100 cells per plate per promoter construct were injected). Eight hours after microinjection of the plasmid (p) DNA, in situ hybridization was performed with a nick-translated fluorescein labeled pGL3$_{Basic}$ probe. The pGL3$_{Basic}$ vector remained in the cytoplasm, whereas the pGL3$_{Basic}$ vector containing the hCol1α2 promoter rapidly entered the nucleus, as evidenced by fluorescent staining. None of the other promoter sequences: osteocalcin, hBSP, Cbfa1/Runx2 and hCol1α1 promoters in the pGL3$_{Basic}$ vector significantly directed nuclear entry. During the eight hour period after injection, cells did not go through mitosis and cell division, confirming that nuclear entry was achieved in the presence of an intact nuclear membrane. This demonstrates the intrinsic nuclear entry activity of osteoblast promoters. Without being bound by theory, it is likely that nuclear entry of the construct containing the pGL3 hCol1α2 nuclear targeting sequence is mediated by a mechanism dependent on nuclear localization signals ("NLS") within the nuclear DNA binding factors that interact with the binding sites within the hCol1α2 sequence.

The pGL3-hCol1α2 region (shown in FIG. 1 as nucleotide positions −267 to +45 relative to the transcription start site) pDNA was injected into the cytoplasm of ROS 17/2.8 osteoblasts and rat skin fibroblasts and analyzed by in situ hybridization eight hours later, as described above. Bright fluorescent staining indicative of the pGL3-hCol1α2 promoter plasmid binding to the fluorescein-labeled pGL3$_{Basic}$ probe was observed. DAPI was used to as a nuclear counterstain. Both stains co-localized in osteoblast nuclei. In contrast, fluorescein staining was observed only in the cytoplasm of fibroblasts. The hCol1α2 promoter entered the nucleus in osteoblasts but not in fibroblasts, demonstrating the osteoblast specificity required for the development of skeletal targeting vectors.

The hCol1α2 promoter also localized to the nuclei of cultures of nontransformed human osteoblasts after microinjection showing that the effect was not species specific. The nuclear import efficiency of hCol1α2 DNA compares favorably to that of the smooth muscle cell specific gamma actin promoter which mediates nuclear import in 30-50% of microinjected smooth muscle cells. This level of nuclear entry demonstrated in vitro translated into efficient gene delivery into smooth muscle cells in vivo. Similar efficiency is expected in vivo. It is also apparent that nuclear entry activity is only demonstrated by a small number of osteoblast promoters and is not common to all natural promoters.

Example 4

Identification of DNA Regulatory Elements in the hCol1α2 Promoter that Bind to Transcription Factors that can Mediate Nuclear Entry To develop a promoter with optimum nuclear entry and transactivation properties, and to minimize the size of the sequence to include only the required regulatory elements, the contribution of each of the putative DNA regulatory elements in the hCol1α2 promoter in the mediation of nuclear entry or basal promoter activity in osteoblasts was determined. The regulatory elements in the hCol1α2 promoter required for basal activity in osteoblasts had not been extensively studied by other laboratories so selection of the control elements to study was based on identification of consensus transcription factor binding sequences (regulatory elements) and on conservation of these sequences across species. Eleven control elements common to human, mouse and rat (FIG. 1) were selected for mutagenesis. Mutations were generated by site directed mutagenesis with the Quick Change Kit (Stratagene). Mutation in any one of the consensus regulatory elements abolished nuclear entry activity while mutations in the control elements either had 1) no effect on basal promoter activity (AP-1, CArG Box, iCAAT), reduced basal promoter activity (Krox 20, E-box, HD binding site) or increased basal promoter activity (NRE, dual AP-2, CME and Mef-2/TATA Box). These results suggested that a combination of control elements that bound to a number of diverse transcription factors in the proximal promoter were involved in osteoblast specific nuclear entry. From these studies it was concluded that optimal nuclear entry activity of the hCol1α2 promoter is obtained when the sequence from −267 to +45 is used intact to construct an osteoblast specific nuclear entry vector.

Example 5

Constructing a Vector with Osteoblast Specific Nuclear Entry Activity that is Expressed Specifically in Osteoblasts The plasmid vector pCMV-GFP (Young et al., Gene Ther. 10:1465-1470, 2003) was used to form the backbone structure of the prototype osteoblast nuclear entry vector (FIG. 2). The CMV promoter in this vector was replaced and the hCol1α2 promoter and was used to drive expression and to provide nuclear entry activity. No convenient restriction enzyme sites surrounded the CMV promoter, thus blunt-end ligation with two purified DNA fragments (vector and insert) were used. The hCol1α2 promoter was removed from the pGL3$_{Basic}$-hCol1α2 vector with EcoRI. The fragment was blunted with Klenow. The CMV promoter was removed from the pCMV-GFP vector with Vsp1 and Nhe I, the sticky ends were blunted. The hCol1α2 promoter fragment and vector were ligated. The GFP coding region was removed with Age I and BsrG1 to leave the multiple cloning site for insertion of any transgene for expression in osteoblasts.

Example 6

Development of a Chimeric Osteoblast Specific Nuclear Entry Molecule from the hCol1α2 and Human Cbfa1/Runx2 Promoter with Robust Expression Specifically in Osteoblasts for In Vivo Applications The region from −304 to +5 of the human (h)Cbfa1/Runx2 gene demonstrated strong basal promoter activity in osteoblasts but did not have intrinsic nuclear entry activity even though the hCol1α2 and hCbfa1/Runx2 have many regulatory elements in common in their proximal promoters.

PCR fragments encompassing a previously described osteoblast specific enhancer region were amplified with primers FP1 (gtttgggctccttcagcatt: SEQ ID NO:6), FP2 (ctgctctacaaatgcttaac: SEQ ID NO:7), RP3 (tggcatccagaaggatatag: SEQ ID NO:8) and RP4 (ctcacaaaaggcttgtggta: SEQ ID NO:9). The enhancer region includes a putative Twist binding E-box element (E-box 2) and an overlapping NFI site (FIG. 3). Wild type hCbfa1/Runx2 promoter or a hCbfa1/Runx2 promoter template with a mutation in E-box-2 to eliminate TWIST binding were used as templates to generate products that included wild type and mutant enhancer elements. The E-box-2 mutation enhanced basal promoter activity.

Figure 5A:
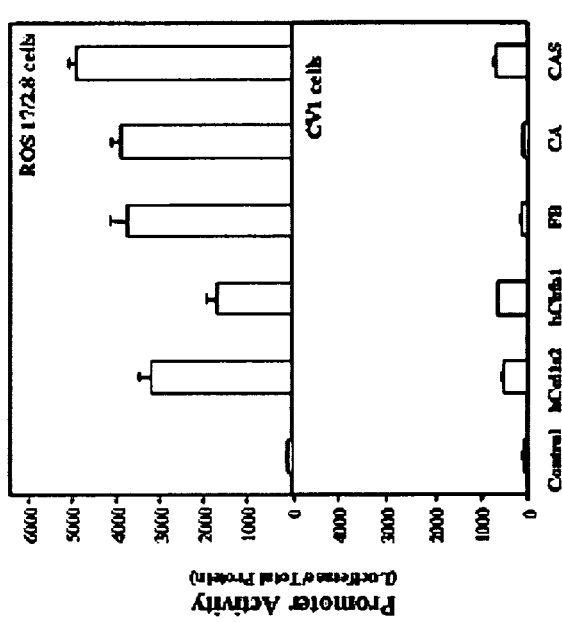
FIGS. 5A-5B are bar graphs demonstrating activation of transcription with the hCol1a2 promoter and the chimeric Cbfa1/Runx2-hCol1α2 promoter constructs.

Different promoter constructs were tested in parallel to determine their effect on basal promoter activity in ROS 17/2.8 cells and CV1 fibroblasts: 1) hCol1α2=−267 to +45 wild type;) type I alpha 2 procollagen promoter; 2) hCbfa1=hCbfa1/Runx2 −304 to +5 wild type promoter; 3) FBCbfa1 (FP1/RP4 primers) enhancer in the reverse orientation placed upstream of the hCol1α2 promoter; 4) CA-two Cbfa1 (FP2/RP3) enhancers with a mutation in the e-box 2 element in the forward orientation placed upstream of the hCol1α2 promoter; and 5) CAS-a single Cbfa1 (FP2/RP3) enhancer in the reverse orientation placed upstream of the hCol1α2 promoter (FIG. 5A).

Figure 5B:
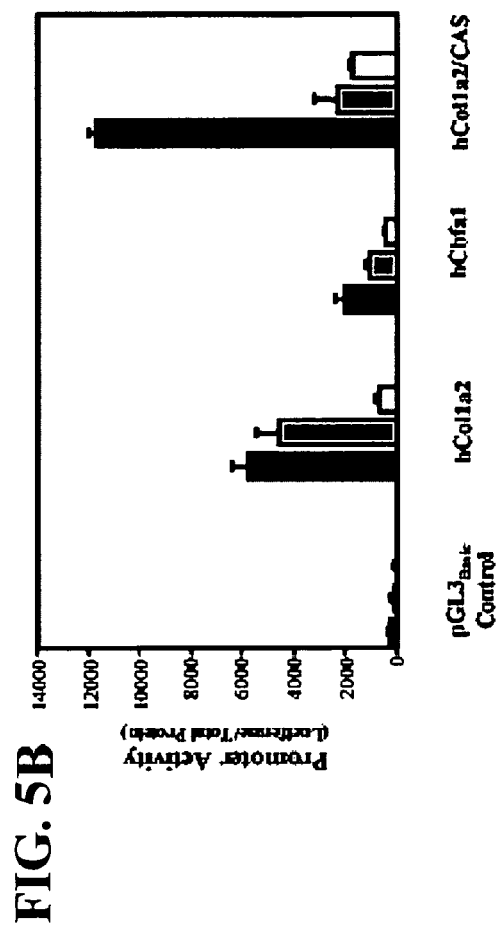

FIG. 5B shows results of testing the hCol1α2, hCbfa1 and CAS chimeric promoters in ROS 17/2.8 cells (solid black bar), in normal rat marrow stromal cells (early osteoblast lineage cells) (grey bar), rat skin fibroblasts (open bar) and rat chrondogenic sarcoma (RCS) cells. Promoter activity was so low in RCS cells that it was not included in the graphs. All promoters were placed in the pGL3$_{Basic}$ vector upstream of the luciferase reporter gene. 50,000 cells per well in a 6 well plate were plated and grown for 48 hours in 10% CS/DMEM. Media was removed and cells were treated with 1 μg of DNA in Effectene/Enhancer (Qiagen) in 1 ml of 10% CS/DMEM overnight at 37° C. Media was changed to 2 ml of 10% CS/DMEM and Luciferase activity and total protein were determined in cell lysates.

All of the Cbfa1/Runx2-derived enhancers (Table 2) stimulated basal promoter activity as shown in FIG. 5A. Robust expression of the hCol1α2, hCbfa1/Runx2 and all of the chimeric promoters occurred in ROS 17/2.8 osteoblasts but not in CV1 fibroblasts. The CAS promoter was further tested in additional cell types including marrow stromal cells, skin fibroblasts and chondrocytes and found to be robustly expressed only in ROS 17/2.8 cells (FIG. 5B). The two chimeric promoters most highly expressed in ROS 17/2.8 osteoblasts had one copy of the FP2/RP3 enhancer in a reverse orientation relative to the hCol1α2 promoter (CAS) or two forward copies of the FP2/RP3 enhancer with a mutation in E-box 2 (CA).

The chimeric hCbfa1/Runx2-hCol1α2 constructs retained nuclear entry activity. Microinjection and in situ hybridization protocols were conducted as described in Example 2. The fluorescent probe bound to plasmid DNA with the hCbfa1/Runx2-hCol1α2 promoter, staining brightly in the nucleus. The Runx2 sequence, added to enhance osteoblast promoter activity, does not alter nuclear entry activity of the osteoblast-specific nuclear entry sequence, in particular the hCol1α2 osteoblast-specific nuclear targeting sequence represented by SEQ ID NO:1.

ers with polymorphisms that do not adversely affect function can be used in the context of nucleic acids for expression in cells of the osteoblast lineage.

Example 7

Preparation of hCol1α2-6TR-NLS-CRE and hRunx2-hCol1α2-6TR-NLS-CRE Constructs

The expression vector prepared for transgenic mice preparation was constructed in several steps starting with the p1411 pTurbo-CRE vector (GENBANK® Accession No. AF334827). In brief, the CMV promoter/enhancer and intron were removed from p1411 pTurbo-CRE by digestion with Sal I and XbaI. The chicken β-actin intron was replaced with the rabbit β-globin intron II (GENBANK® Accession No. V00882). The rabbit β-globin intron was synthesized by PCR to contain a 5' SalI site and a 3'XbaI site using primers: cgtcgactccggatcgatcctgagaa (SEQ ID NO:10) and gtcta-

TABLE 2 hRunx2-hCol1α2 chimeric promoter constructs

| Name of hRunx2 enhancer-pGL3$_{Basic}$ vector | Primer set used to prepare hRunx2 Enhancer | pGL3-hRunx2 Template | Number of Copies of hRunx2 enhancer | Effect of enhancer on transcription in ROS cells (Fold increase over hCol1α2 control) | Orientation of Enhancer Element |
|---|---|---|---|---|---|
| CAS | FP2/RP3 FP2: RP3: | Wild Type | 1 | 2 | E E ← → |
| DC | FP2/RP3 | Wild Type | 1 | 1.3 | E E → → |
| FB | FP1/RP4 FP1: RP4: | Wild type | 1 | 1.5 | E ← → |
| CA | FP2/RP3 | Twist Box 2 Mut | 2 | 2.5 | E E →→ → |

E = wild type AT-rich E-box control elements.
Bold arrow = hCol1α2 promoter (−267 to +45).
Arrows indicate the direction of sequences in the vector with respect to the direction of the luciferase transgene coding sequence (to the right of the hCol1α2 promoter). Promoter enhancer activity is normalized to activity of a pGL3$_{Basic}$ vector containing only the hCol1α2 promoter.

SEQ ID NO:1 is identical to the sequences in the NCBI gene bank with the following Accession numbers: NM_000089.3; AC002074.2; AF004877.1/AF004877; and AB004317.1.

The sequences defining the promoter region of the human Cbfa1/Runx2 gene are highly variable because of the presence of multiple SNPs (Single Nucleotide Polymorphisms) and/or length polymorphisms. The sequence variations can reflect differences in the DNA structure of individuals or SNPs, or reflect the increasing accuracy of the sequencing technology. The sequence used herein to prepare the enhancer of the present disclosure was obtained by PCR using an anomyous DNA sample of an individual with normal bone density. The sequence generated thereby is not identical with any of the three entries in the NCBI database, AB013356.1, AY090738.1, or AL096865.28/HSJ244F24, due to different sets of SNPs. While the sequence used herein reflects the donor individual's specific combination of SNPs in the sequence, reference to the three data base entries clearly identifies the places in the DNA sequence where the SNPs occur. Any of these sequences or other Cbfa1/Runx2 promotgataaccagcacgttgcccagg (SEQ ID NO:11) and the pcDNA6/TR vector DNA (Invitrogen) as a template. The p1411Turbo-CRE (ΔSalI/XbaI) vector was ligated to the SalI-Rabbitβ-globin intron II-XbaI fragment and the ligated product, p1411 (ΔSalI/XbaI)-6TR-NLS-CRE, was transformed into bacteria. Clones were identified that contained the rabbit β-globin intron II in place of the CMV enhancer/chicken β-actin promoter, start of transcription and intron I. The Sal I site at the 5' end of the 6TR intron was preserved for introduction of the hCol1α2 or the hRunx2-hCol1α2 promoters.

Figure 6A:
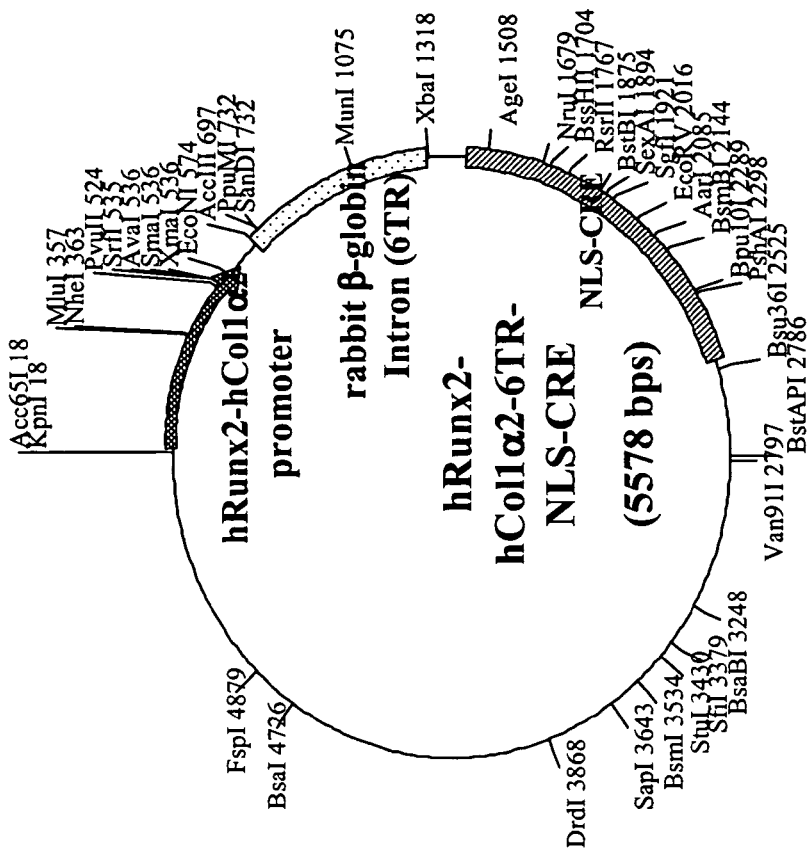
FIGS. 6A-6B are schematic illustrations of the hCol1α2-6TR-NLS-CRE and hRunx2-hCol1α2-6TR-NLS-CRE plasmids, respectively.

The hCol1α2 promoter, transcription start site and 45 bp of 5' untranslated region (−312 to +45) was removed from the pGL3$_{Basic}$ vector with EcoRI. The Eco RI sites were filled in with Klenow to produce a blunt-ended product. The p1411 (ΔSalI/XbaI)-6TR-NLS-CRE vector was cut with Sal I, the Sal I sites were similarly blunted, and the hCol1α2 promoter fragment and vector were ligated to produce the hCol1α2-6TR-NLS-CRE vector (FIG. 6A). After transformation into bacteria, clone hCol1α2-6TR-NLS-CRE, which had the hCol1α2 promoter sequence in the correct forward direction, was identified. Additional clones containing the hCol1α2 promoter in a reverse orientation relative to NLS-CRE that did not expess the CRE recombinase served as a negative control.

To prepare the hRunx2-hCol1α2-6TR-NLS-CRE construct, a Sal I site was introduced into the 5' and 3' ends of the hRunx2-hCol1α2 promoter by PCR using primers: ggtcgacctctatcgataggtaccctag (SEQ ID NO:12) and gcgtcgacgccagtacctccaacttagc (SEQ ID NO:13) with the pGL3$_{Basic}$ plasmid, CA (Table 2) as a template.

Figure 6B:
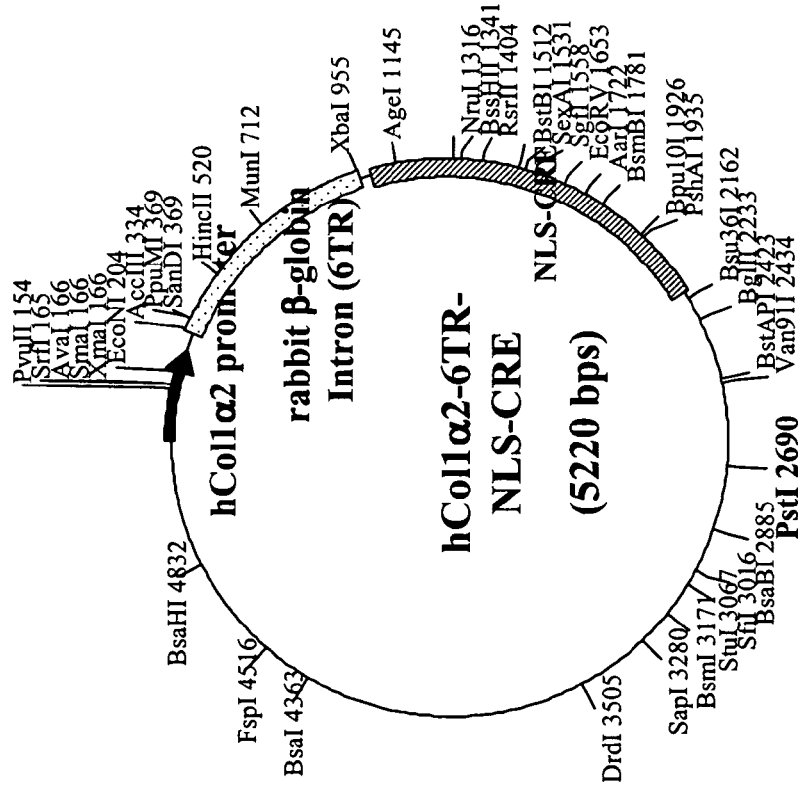

The PCR generated promoter fragment was cloned into pCR-Blunt TOPO and removed from this vector with Sal I. The p1411 (ΔSalI/XbaI)-6TR-NLS-CRE vector (with the rabbit β-globin intron II introduced into the Sal I and XbaI sites of the p1411 vector) was cut with Sal I and ligated to the Sal I hRunx2-hCol1α2 promoter fragment to produce an hRunx2-hCol1α2-6TR-NLS-CRE construct (FIG. 6B). Ligated products were introduced into bacteria and clones were identified with the hRunx2 enhancer-hCol1α2 promoter in either orientation. Constructs with the promoter in the correct orientation were selected for in vitro testing and for development of transgenic mice.

Plasmid DNA was replicated in bacteria and purified according to using an EndoFree Plasmid Maxi Kit from Qiagen. The 5.2 kb hCol1α2-6TR-NLS-CRE plasmid DNA was linearized with Pst I and the overhangs were blunted with Klenow. The 5.6 kb hRunx2-hCol1α2-6TR-NLS-Cre plasmid DNA was linearized with Stu I prior to fill-in synthesis with Klenow. The linear DNA isolated from an agarose gel and extracted using a Qiaquick Gel Extraction Kit (Qiagen). Each of the linearized DNAs was further purified by CsCl centrifugation prior to mouse oocyte injection.

Example 8

Expression of Osteoblast Specific CRE Recombinase in R26R Calvarial Osteoblasts

Cells were isolated from newborn R26R calvaria using collagenase as previously described (Linkhart et al., *J Bone Miner Res* 14:3946, 1999) and were cultured in a MEM/10% fetal bovine serum (FBS). DNA was isolated from confluent cell cultures by proteinase K digestion in 0.1 M NaCl, 50 mM Tris, 0.1 mM EDTA, 1% SDS pH 8.0 followed by phenol/chloroform/isoamyl alcohol extraction and isopropanol precipitation.

Calvarial cells isolated from a R26R mouse were plated in 6 well plates (100,000/well) in two mls of DMEM/10% CS overnight. DNA (2 μg) corresponding to the p1411 pTurbo-CRE control, hCol1α2-6TR-NLS-CRE, hCol1α2 (reverse)-6TR-NLS-CRE or promoterless p1411 pTurbo-CRE (ΔSalI/XbaI) was individually transfected into R26R calvarial cells 24 hours after plating, with 5 μl of Effectene, 4 μl of Enhancer in 1 ml of DMEM/10% CS for 18-22 hours. The medium was replaced with 2 ml of DMEM/10% CS, and cells were incubated for an additional 48 hours at 37° C. in a humidified incubator with 95% air/5% CO$_2$. Media was removed and cells were stained for β-gal activity.

A β-gal staining procedure was derived from methods from an Invitrogen staining kit. In brief, the medium was removed and cells were rinsed 1×PBS. The cells were then fixed with 1 ml of Fixative Solution (2% formaldehyde, 0.2% glutaraldehyde in 1×PBS) at room temperature. The cells were rinsed twice with 2.5 ml 1×PBS, and 1 ml of staining solution (1 mg/ml X-gal in 4 mM potassium ferricyanide, 4 mM potassium ferrocyanide, 2 mM magnesium chloride, 1×PBS) was added to each well and cells were incubated at 37° C. in a humidified incubator for several hours. The stained cells were overlayed with 70% glycerol and stored at 4° C. prior to analysis. Cells were viewed with a 30× objective and photographed with an Olympus IX-70 microscope with Olympus 1.3 megapixel CCD camera and Megafire 2.1C imaging software. Only cells transfected with the hCol1α2-6TR-NLS-CRE vector produced β-gal activity. The β-gal activity was found in groups of calvarial cells that had begun to form bone nodule like structures.

This in vitro test of the first hCol1α2-6TR-NLS-CRE vector indicated that the engineered construct could robustly produce CRE recombinase in cells of the osteoblast lineage.

Example 9

Bone Targeting of Transgenes by an Osteoblast-Specific Nuclear Targeting Sequence The linearized and CsCl centrifugation purified linear hCol1α2-6TR-NLS-CRE or hRunx-2-hCol1α2-6TR-NLS-CRE nucleic acids were injected into fertilized B6D2F1 mouse oocytes. The injected oocytes were introduced into the uteri of pseudopregnant female mice and carried to term. Two founders (designated 522 and 508) were identified with the hCol1α2-6TR-NLS-CRE transgene. Four founders (designated 904, 917, 920 and 922) were identified with the hRunx2-hCol1α2-6TR-NLS-CRE transgene. These founders consistently transmitted the transgene to progeny. The founder animals were bred with C57BL/6 mice to create F1s in a more homogeneous genetic background, and to ROSA26 indicator mice (Soriano, *Nat Genet.* 21:70-1, 1999) to study the specificity of transgene expression. A transgenic mouse in which CRE expression is driven by 2.3 kb of the mouse typeI α1 procollagen (mCol1α1) promoter, which has been shown to conditionally express CRE in mature osteocytes and osteoblast lineage cells (Dacquin et al., *Dev Dyn.* 224:245-51, 2002) served as a positive control after crossing with ROSA26 mice.

Progeny with the CRE recombinase gene were identified by PCR analysis of the DNA isolated from ear or tail tissue using a DNeasy Tissue kit from Qiagen according to the manufacturer's directions. Several primer sets were developed for genotyping mice with the transgenes disclosed herein. These primers are provided in Table 3. Separate primer sets were established to identify the hCol1α2-6TR-NLS-CRE ($B_1$), the hRunx2-hCol1α2-6TR-NLS-CRE ($B_2$) and the mouse (m) Col1α1-CRE genotype ($B_3$). $C_1$ and $C_2$ CRE primers were used interchangeably. Three primers producing PCR products of 300 and 600 bp were used concurrently to identify the floxed-α-galactosidase (gal) gene indicative of the R26R genotype. The GAPDH primer set was used to evaluate the integrity and quantity of genomic DNA preparations made from tail samples using a Qiagen extraction kit.

TABLE 3

Transgenic Mouse Genotyping Primers

| Gene | Primer Sequence (5'-3': forward & reverse primer) | SEQ ID NO: | Product Size (bp) | Accession # (position in sequence) |
|---|---|---|---|---|
| A. GAPDH | tggccttccgtgttcctacc<br>ttactccttggaggccatgt | SEQ ID NO: 14<br>SEQ ID NO: 15 | 316 | BC083065.1 |
| B₁. hCol1α2 promoter-rβ-globin intron | caccacggcagcaggaggttt<br>ggcaggatgatgaccaggat | SEQ ID NO: 16<br>SEQ ID NO: 17 | 542 | AF004877.1-<br>OCBGLO |
| B₂ hRunx2-hCol1α2 promoter-rβ-globin intron | gatcttacgcgtgctagccc<br>ggcaggatgatgaccaggat | SEQ ID NO: 18<br>SEQ ID NO: 19 | 832 | AY487822.1<br>(pGL3$_{Basic}$)<br>OCBGLO |
| B₃. mCol1α1 | cacactgctgctcatcactt<br>gctaagcagatgtgcctgtt | SEQ ID NO: 20<br>SEQ ID NO: 21 | 274 | MMCOL1A11 |
| C1. CRE recombinase | tgcctgcattaccggtcgat<br>ggaccgacgatgaagcatgt | SEQ ID NO: 22<br>SEQ ID NO: 23 | 273 | MYP1CRE<br>AF334827.1 (p1411 pTurboCre) |
| C2 CRE recombinase | caagctggtggctggaccaat<br>catatgtccttccgagtgagag | SEQ ID NO: 24<br>SEQ ID NO: 25 | 338 | AF334827.1 (p1411 pTurboCre) |
| D. ROSA26 Reporter Gene | cccaaagtcgctctgagttgttat<br>ggagcgggagaaatggatatg<br>gcgaagagtttgtcctcaacc | SEQ ID NO: 26<br>SEQ ID NO: 27<br>SEQ ID NO: 28 | 600<br>300 | Soriano, Nat Genet.<br>21:70-1, 1999 | r = rabbit, m = mouse, h = human

PCR reactions were conducted with 3 µl of genomic DNA (20-80 ng DNA), 1 µl (5 units of Taq Polymerase from Fisher), 10 pmoles forward and 10 pmoles reverse primer, 1 µl (2.5 mM each dNTPs from Promega), 5 µl of 10 Buffer A (500 mM KCl, 15 mM MgCl₂, 100 mM Tris-HCl pH 9.0) and molecular grade water to a final volume of 50 µl. For primers sets A, B and C, genotyping was conducted with the following PCR cycling parameters: a hot start at 95° C. for 5 minutes, thirty cycles at 95° C. for 1 minute, 60° C. 1 minute and 72° C. for 1 minute; 10 minutes at 72° C., 10 minutes at 4° C. and held at 10° C. overnight. For primer set D, to identify the R26R genotype, the PCR cycling parameters were 95° C. for 5 minutes, 30 cycles of 95° C. for 1 minute, 52° C. 1 minute and 1 minute at 72° C. then 72° C. for 10 minutes, 10 minutes at 4° C. and overnight at 10° C.

ROSA26 mice have the ROSA26 (R26R) gene incorporated into their genomes. The transgene is a floxed β-galactosidase (gal) indicator cDNA that does not express β-gal until CRE removes a floxed stuffer DNA sequence. Expression is driven by a natural mouse promoter that is active in newborn and young animals (Soriano, Nat Genet. 21:70-1, 1999). Homozygous mice were used for breeding.

Table 4 summarizes the genotype and phenotype of the mice produced after crossing ROSA26 to founders (904, 917, 920 and 922) or to the F1 progeny of founders 508 and 522. Crosses were also produced with mCol1α1-CRE transgenic mice.

TABLE 4 hCol1α2-6TR-CRE, hRunx2-hCol1α2-6TR-CRE and mCol1α1-CRE expressing transgenic mouse lines

| Gene construct used to create transgenic mice | Founders (Mouse #) | Founder X C57BL/6 (F1) | Founder or F1 X ROSA26 (Mouse #) | ROSA26 (mouse #) | Phenotype |
|---|---|---|---|---|---|
| hCol1α2-6TR-NLS-CRE | 508 | | | | |
| 23 pups | | F1A5 | 587, 588, 589 590, 591, 592, 593 | 826 | Blue stained femur in 2-3 month old animals |
| | | F1A5 | male, female | 822 | Blue stained femur |
| | | F1A5 | P12, P13, P14, P15, P16, P17 | 579 | Blue stained femur and calvaria in 2-3 week old animals |
| | 522 | | | | |
| | | F1N22 | 555, 586 550, 551, 554, 553, 580, 574, 584, 582 | 827 | Blue stained femur in 2-3 month old animals |

TABLE 4-continued hColla2-6TR-CRE, hRunx2-hColla2-6TR-CRE and mColla1-CRE expressing transgenic mouse lines

| Gene construct used to create transgenic mice | Founders (Mouse #) | Founder X C57BL/6 (F1) | Founder or F1 X ROSA26 (Mouse #) | ROSA26 (mouse #) | Phenotype |
|---|---|---|---|---|---|
| hRunx2 (mut E-Box 2)-hColla2-6TR-NLS-CRE 21 pups | 904 | | 528, 530, 532, 534, 536, 538, 542, 549, 559 | 753 | Blue stained femur and cavaria in 2-3 month old animals |
| | 917 | | 527, 531, 533, 540, 740, 742, 744, 746, 748 | 826 | |
| | 920 | | 569, 571, 573, 576, 578 P1, P2, P3, P4, P5, P6, P7, P8, P9 | 751 | Blue stained femurs and calvaria in 2 week to 2 month old animals |
| | 922 | | 515, 521, 523 558, 560, 564, 4C, 44 | 579 | Blue stained femur and calvaria |
| | 922 | | 678, 680, 681, 683, 687, 693, 696 | 579 | Blue stained femur and calvaria |
| mColla1-CRE | 42 | | 4-1, 2-1, 3-1 | 579 | Blue stained calvaria and femurs in 2 month old animals |
| | | | 544, 562 | 579 | Blue stained calvaria and femurs |
| | | | P10, P11 | 579 | |

Even numbered animals are females and odd numbered animals are males.
Bolded numbers indicate the presence of blue stained bones.
Mouse # 579 = ROSA26 from UCLA;
Mice #s 751, 753, 826 and 827 = ROSA26 from Jackson Labs.

Tissue specificity of CRE recombinase expression was confirmed in transgenic mice by PCR. Macroscopic examination of tissues from hColla2-6TR-NLS-CRE X ROSA26 mice revealed β-gal activity in skeletal (femur) tissue. In contrast, samples of tissues from brain, heart skeletal muscle, liver and kidney did not stain blue indicating that CRE recombinase was not highly expressed in these tissues. Similar results were observed in mice expressing the CRE recombinase under the control of the hRunx2-hColla2 promoter. Transgene negative littermates did not exhibit staining in any tissues examined. Mice expressing CRE recombinase driven by the mColla1 promoter also activated β-galactosidase (β-gal) expression in skeletal tissues when mice were crossed to ROSA26 indicator mice.

β-gal activity was also confirmed microscopically. Skeletal and other stained tissues from the hColla2-6TR-NLS-CRE X ROSA26 mice were evaluated for β-gal activity by microscropy. β-gal activity is detected as blue staining after exposing the tissues to X-gal, which is converted to a visible product by β-gal. Tissues were counter stained with nuclear fast red to identify structures. Osteoblast lineage cells on the bone surface and osteocytes embedded in bone near the growth plate in femoral samples stained blue indicating expression of CRE and β-gal activity. Blue stain was not observed in soft tissue samples or in skeletal tissues from mice that did not express the collagen driven CRE recombinase transgene. In younger animals blue staining of osteoblast lineage cells was also noted in calvarial samples (Table 4). Blue stained osteoblasts on the bone surface and blue stained osteocytes embedded in bone were noted. Similarly, microscopic examination of tissues from hRunx2-hColla2-6TR-NLS-CRE X ROSA26 mice showed β-gal activity as evidenced by blue staining in osteoblasts lining the bone surface and in embedded osteocytes in both calvaria and femur samples. In sporadic samples a small group of cells in brain tissue stained blue but only in older animals. Low levels of collagen synthesis have been noted previously in brain tissue. Staining was not observed in soft tissues of the same mice. Blue staining was not observed in bone samples of transgene negative littermate controls.

In summary, β-gal staining was observed in skeletal tissue in mice expressing NLS-CRE from both the hColla2 and hRunx2-hColla2 promoters. CRE expression driven by both type I procollagen promoters was noted predominantly in osteoblast lineage cells and not in the cells of other tissues, demonstrating the tissue specificity of these regulatory sequences. Stronger blue staining indicative of more robust CRE recombinase expression was observed with the Runx2-hColla2 promoter and was macroscropically visible in both femur and calvaria samples after X-gal staining. Expression of CRE from this type I procollagen/Runx2 combination promoter became more pronounced as the animals aged.

Based on these results it is evident that the hRunx2-hColla2 and hColla2 promoters contain an osteoblast specific nuclear entry sequence and are correctly expressed in skeletal tissues in vivo.

While the invention has been disclosed in certain embodiments, the scope of the invention is not intended to be limited thereby and such other embodiments as can be suggested by the teachings herein are particularly reserved, especially as they fall within the breadth and scope of the following claims.

We claim:

1. An isolated or recombinant nucleic acid comprising an expressible heterologous polynucleotide sequence operably linked to a polynucleotide sequence comprising an osteoblast-specific nuclear targeting sequence, wherein the osteoblast-specific nuclear targeting sequence consists of a polynucleotide sequence at least 95% identical to SEQ ID NO: 1, wherein the polynucleotide sequence comprising the osteoblast-specific nuclear targeting sequence is contiguous on either side with polynucleotide sequences with which it is not contiguous in the human genome, and wherein the osteoblast-specific nuclear targeting sequence mediates osteoblast-specific nuclear entry.

2. The isolated or recombinant nucleic acid of claim 1, wherein the osteoblast-specific nuclear targeting sequence consists of SEQ ID NO: 1.

3. The isolated or recombinant nucleic acid of claim 1, wherein the nucleic acid further comprises a promoter.

4. The isolated or recombinant nucleic acid of claim 1, further comprising an osteoblast-specific enhancer, wherein said enhancer is operably linked to the expressible heterologous polynucleotide sequence.

5. A vector comprising the nucleic acid of claim 1.

6. An isolated host cell comprising the nucleic acid of claim 1.

7. The host cell of claim 6, wherein the host cell is a cell of the osteoblast lineage.

8. A kit comprising the nucleic acid of claim 1 and at least one of a control nucleic acid, a buffer, an osteoblast lineage cell and a set of instructions.

9. The isolated or recombinant nucleic acid of claim 1, further comprising one or more protein binding site regulatory elements selected from the group consisting of AP-1, NRE, CarG Box, Krox 20, E-box, AP-2, iCAAT Box, CME, TATA Box/Mef-2 and Homeobox Protein binding site regulatory elements.

10. The isolated or recombinant nucleic acid of claim 1, wherein the osteoblast-specific nuclear targeting sequence consists of a polynucleotide sequence at least 98% identical to SEQ ID NO: 1.

* * * * *

UNITED STATES PATENT AND TRADEMARK OFFICE
CERTIFICATE OF CORRECTION

PATENT NO. : 7,741,113 B2  
APPLICATION NO. : 11/410579  
DATED : June 22, 2010  
INVENTOR(S) : Strong et al.

Page 1 of 2

It is certified that error appears in the above-identified patent and that said Letters Patent is hereby corrected as shown below:

Title page, item (56) Other Publications:

Cover page, column 2, line 3, "(JBC" should read --JBC--

Cover page, column 2, line 4, "(Connective" should read --Connective--

Cover page, column 2, line 5, "(Journal" should read --Journal--

Cover page, column 2, line 7, "(Gene" should read --Gene--

Cover page, column 2, line 8, "[PNAS 98(15): 8650-8655, 2001)]." should read --PNAS 98(15): 8650-8655, 2001.--

Column 1, lines 15-21, "Research for the present disclosure was supported by grants from the National Medical Technology Testbed, and a Special Congressional Award to the Musculoskeletal Disease Center at the VA Loma Linda Healthcare System and was conducted in part at research facilities within the VA Loma Linda Healthcare System. Accordingly, the United States government has certain rights in the invention." should read --This invention was made with government support under Grant No. DAMD17-97-2-7016 awarded by the Army MRMC. The government has certain rights in the invention.--

Column 8, line 17, "in of bone" should read --in bone--

Column 11, line 56, "3'regions" should read --3' regions--

Column 15, line 7, "acids, lacking" should read --acids lacking--

Column 16, line 5, "molecule The" should read --molecule. The--

Column 16, line 18, "gene)" should read --gene.--

Column 16, line 55, "hColl a2" should read --hCollα2--

Signed and Sealed this

Twenty-third Day of November, 2010

David J. Kappos  
*Director of the United States Patent and Trademark Office*

CERTIFICATE OF CORRECTION (continued)
U.S. Pat. No. 7,741,113 B2

Column 17, line 18, "hColla2" should read --hCollα2--

Column 19, line 64, "99:42564261" should read --99:4256-4261--

Column 23, line 41, "hColla2" should read --hCollα2--

Column 26, line 59, "genes" should read --genes.--

Column 31, line 30, "Carrell" should read --Carell--

Column 32, line 65, "hColla2" should read --hCollα2--

Column 34, line 36, "plasmid (P) DNA" should read --plasmid (p) DNA--